(12) United States Patent
Ramot et al.

(10) Patent No.: US 10,576,116 B2
(45) Date of Patent: Mar. 3, 2020

(54) ASTERISCUS GRAVEOLENS EXTRACTS AND USE THEREOF

(71) Applicant: I.B.R. Israeli Biotechnology Research Ltd., Yavne (IL)

(72) Inventors: Ofir Ramot, Ashdod (IL); Fabien Havas, Bnei Dkalim (IL); Eyal Kalo, Nes-Ziona (IL); Liki Von Oppen-Bezalel, Berlin (DE); Raffi Arnon, Rehovot (IL); Olga Ben-Chitrit, Ashdod (IL); Inon Perry, Tel Aviv (IL)

(73) Assignee: I.B.R. Israeli Biotechnology Research Ltd., Yavne (IL)

( * ) Notice: Subject to any disclaimer, the term of this patent is extended or adjusted under 35 U.S.C. 154(b) by 0 days.

(21) Appl. No.: 15/547,385

(22) PCT Filed: Feb. 1, 2016

(86) PCT No.: PCT/IL2016/050105
§ 371 (c)(1),
(2) Date: Jul. 28, 2017

(87) PCT Pub. No.: WO2016/125146
PCT Pub. Date: Aug. 11, 2016

(65) Prior Publication Data
US 2018/0021394 A1 Jan. 25, 2018

Related U.S. Application Data

(60) Provisional application No. 62/110,634, filed on Feb. 2, 2015, provisional application No. 62/146,435, filed on Apr. 13, 2015.

(51) Int. Cl.
| | |
|---|---|
| *A61K 36/28* | (2006.01) |
| *A61K 9/00* | (2006.01) |
| *A61Q 19/08* | (2006.01) |
| *A61K 8/9789* | (2017.01) |
| *A61Q 19/00* | (2006.01) |
| *A61K 47/10* | (2017.01) |
| *A61K 9/08* | (2006.01) |
| *A61Q 11/00* | (2006.01) |
| *A61K 8/97* | (2017.01) |
| *A61Q 17/00* | (2006.01) |

(52) U.S. Cl.
CPC ............... *A61K 36/28* (2013.01); *A61K 8/97* (2013.01); *A61K 8/9789* (2017.08); *A61K 9/0014* (2013.01); *A61K 9/08* (2013.01); *A61K 47/10* (2013.01); *A61Q 11/00* (2013.01); *A61Q 17/00* (2013.01); *A61Q 19/00* (2013.01); *A61Q 19/08* (2013.01); *A61K 2236/00* (2013.01); *A61K 2236/331* (2013.01); *A61K 2236/333* (2013.01)

(58) Field of Classification Search
None
See application file for complete search history.

(56) References Cited

U.S. PATENT DOCUMENTS

| 8,846,114 B1 * | 9/2014 | Makela | A61K 31/351 |
| | | | 424/725 |
| 2007/0122492 A1 * | 5/2007 | Behr | A61Q 17/04 |
| | | | 424/725 |

OTHER PUBLICATIONS

International Search Report and Written Opinion from International Application No. PCT/IL2016/050105 dated May 18, 2016.
«http://www.cosmeticdesign-asia.com/Product-innovations/IBR-Pristinizer-R-Shields-against-pollution» Mar. 16, 2015.
«http://israel.agrisupportonline.com/news/csv/csvread.pl?show=4499&mytemplate=tp2» Jan. 2, 2014.
Alilou et al., "Antifungal and Antioxidant Activity of *Asteriscus graveolens* subsp. odorus Essential Oil"; Journal of Natural Sciences Research, vol. 4, no. 10, 2014.
Alilou et al., "Screening phytochimique et identification spectroscopique des flavonoides d'Asteriscusgraveolenssubsp. odorus", Afrique Science 10(3), 2014, pp. 316-328.
Ofir et al., Israel-Jordan Research Cooperation Conference—Dead Sea 6-7.12.2012.

* cited by examiner

*Primary Examiner* — Robert A Wax
*Assistant Examiner* — Danah Al-Awadi
(74) *Attorney, Agent, or Firm* — Greenberg Traurig, LLP

(57) ABSTRACT

The present invention relates to extracts derived from plants and/or fractions thereof, compositions comprising same and use thereof in protecting tissues from damages caused by exogenous toxins. In particular, the present invention relates to polar extract and/or fraction thereof derived from *Asteriscus graveolens*, compositions comprising same and use thereof in protecting tissues comprising epithelial cell from the deleterious effect of exogenous toxins, particularly toxins originating from environmental pollution.

14 Claims, 6 Drawing Sheets

*ASTERISCUS GRAVEOLENS* EXTRACTS AND USE THEREOF

RELATED APPLICATIONS

This application is a national phase filing under 35 USC 371 of International Application No. PCT/IL2016/050105, filed on Feb. 1, 2016, which claims priority of U.S. Patent Application No. 62/110,634, filed Feb. 2, 2015, and U.S. Patent Application No. 62/146,435, filed Apr. 13, 2015, the entirety of which are incorporated herein by reference for all purposes.

FIELD OF THE INVENTION

The present invention relates to extracts derived from plants and/or fractions thereof, compositions comprising same and use thereof in protecting tissues from damages caused by exogenous toxins, particularly to polar solvent extract and/or fraction thereof derived from *Asteriscus graveolens* and compositions comprising same for protecting tissues comprising epithelial cell from the deleterious effect of exogenous toxins, particularly of toxins originating from environmental pollution.

BACKGROUND OF THE INVENTION

Epithelium is one of the four basic types of animal tissues, along with connective tissue, muscle tissue and nervous tissue. Epithelial tissues line surfaces and cavities throughout the body. Epithelium forms part of both the outside surface (skin) and the inside cavities and lumen of mammalian bodies. Functions of epithelial cells include protection, detection of sensation, selective absorption, secretion and transcellular transport.

The skin comprises stratified squamous, keratinized epithelial cells and viable keratinocytes among other cell types. Tissues lining the inside of the mouth, the esophagus and part of the rectum are composed of non-keratinized stratified squamous epithelium. Other surfaces that separate body cavities from the outside environment are padded by simple squamous, columnar, or pseudo-stratified epithelial cells. Other epithelial cells line the inside of the lungs, the gastrointestinal tract, the reproductive and urinary tracts, and make up the exocrine and endocrine glands. The outer surface of the cornea is covered with fast-growing, easily regenerated epithelial cells.

In these organs and tissues, the epithelium serves as part of the protective barrier against harmful physical forces, chemicals, pollutants, pathogens and other undesired agents. All of these exogenous aggravations must challenge the epithelium before entering into the body.

Pollution born toxins have detrimental effect on the health of cells and tissues and on organs comprising same. Pollution may be caused by a vast number of a variety of factors, including, for example, indoor pollution resulting from cigarette smoke, cleaning products and dust, and outdoor pollution including engine smoke, industrial waste and carbon monoxide.

Toxic buildup is known to impair an organ's normal physiologic functions. The constant, sometimes daily exposure to environmental toxins leads to accumulated damage in the cells of all exposed organs. Common cellular mechanism by which most pollutants exert their adverse effects include their ability to act directly as pro-oxidants of lipids and proteins, form DNA adducts, DNA breakage or mutations or to act as free radicals generators, promoting oxidative stress and the induction of inflammatory responses.

Free radicals (reactive oxygen and nitrogen species) are harmful to cellular lipids, proteins, and nuclear- or mitochondrial-DNA, inhibiting their normal function. In addition, they can interfere with signaling pathways within cells. In eukaryotic aerobic organisms including humans, free radicals are continuously generated during normal metabolism and in response to exogenous environmental exposures (e.g. irradiation, cigarette smoke, metals and ozone). A state of oxidative stress occurs when the organism defense mechanisms are overwhelmed leading to an increase in the free radical concentration. This oxidative stress has been shown to be linked with poor appearance and premature aging of the skin. Oxidative stress has also been implicated in a wide variety of degenerative diseases such as atherosclerosis, heart attacks, stroke, chronic inflammatory diseases (rheumatoid arthritis), cataract, central nervous system disorders (Parkinson and Alzheimer's diseases), age related disorders and cancer.

Pollutants mainly reach mammalian tissues via dermal contact, inhalation and ingestion of contaminated products. Air and soil pollution contributes, to a great extent, to the contamination of food and water, such that ingestion is also a route of pollutant intake. Pollutants deposited in the gastrointestinal and respiratory tracts may be absorbed by the epithelial cells such that toxic substances appear in the general circulation and accumulate in different tissues.

The link between exposure to certain substances and epithelium damage is universally accepted. For example, formaldehyde is now recognized worldwide as both a carcinogen and a skin sensitizer. Another example is the pollutant chemicals found in tobacco smoke. Cigarette smoke contains over 4,700 chemical compounds of which about 60 have been designated as carcinogenic. People who smoke on a regular basis are prone to a damage of tissue comprising epithelial cells, particularly of the lung, oral cavity and skin. Aging processes of smoker's skin are also accelerated.

All types of pollution, at high concentration, can affect mammalian airways and gastrointestinal tract. Nevertheless, similar effects are also observed with long-term exposure to lower pollutant concentrations. Symptoms such as nose and throat irritation, followed by bronchoconstriction and dyspnoea, especially in asthmatic individuals, are usually experienced after exposure to increased levels of sulphur dioxide, nitrogen oxides, and certain heavy metals such as arsenic, nickel or vanadium. Air pollutants such as nitrogen oxides increase the susceptibility to respiratory infections. Chronic exposure to ozone and certain heavy metals reduces lung function, while the later are also responsible for asthma, emphysema, and even lung cancer. Emphysema-like lesions have also been observed in mice exposed to nitrogen dioxide The epithelium possesses a limited active toxin defense including physical removal of exogenous toxins. Exemplary routes include the natural expulsion of contaminated cells as part of skin's organic turn-over and dissolving of toxins from interstitial spaces and transferring these back onto the surface via sweat. However, the natural defense mechanisms against toxins do not provide full protection.

Toxins that have not been physically removed may be metabolized within the epithelium. In recent years it has been demonstrated that human epithelium cells express various Cytochrome P450 (CYP) enzymes, including such that are responsible specifically for metabolism of exogenous toxins within various types of epithelial cells. The resulting metabolites may potentially also damage the epithelium and body. Defense against skin toxins depends on several factors, including behavioral routines (i.e., avoidance of exposure, diet) and use of traditional medicine, therapeutic and/or cosmetic products.

Traditional medicine has long appreciated the negative effect of toxin deposit on health and wellbeing and practices detoxification of the body as standard treatment for many diseases and disorders. Similar practices, with some variations, are very commonly self-implemented by the public. These detoxification processes focus on reducing the exposure to toxins and increasing removal of toxins from the body.

Skin is the largest and the most exposed organ of the body comprising epithelial tissues. Skin has numerous functions, the primary function being a protective barrier against harmful physical forces, chemicals, pollutants, pathogens and other undesired agents. The skin consists of three main layers: the epidermis, the outermost layer of skin, which provides a waterproof barrier and creates the skin tone; the dermis, which contains tough connective tissue, hair follicles, and sweat glands; and the deeper subcutaneous tissue (hypodermis), which is made of fat and connective tissue. The epidermis is further subdivided into several layers: the stratum corneum, the stratum granulosum, the stratum spinosum, and the stratum basale.

The genus *Asteriscus* (Tribe Inuleae, family Asteraceae) consists of eight species and five sub-species, the morphology, phylogeny, and phytogeography of which have been studied. *Asteriscus graveolens* (Forssk.) Less., has the synonyms *Bubonium graveolens, Odontospermum graveolens*, or *Nauplius graveolens*. This species, an endemic herbaceous medicinal aromatic plant, extends from North Africa to the desert regions of Asia. It has been used in Sahara folk medicine as a stomachic, for treating fever, gastrointestinal tract complaints, headache and bronchitis, and as an anti-inflammatory agent. The chemical composition of *A. graveolens* essential oils was recently described by Cristofari et al. (Cristofari G et al. 2012. Chemistry and Biodiversity 9:727-738). Traditional Chinese medicine preparations comprising a mixture of dried plant material including plants of the Asteraceae family, particularly of *A. pseudosciaenae* have been disclosed (for example, Chinese Applications No. CN104208618, CN104274770, CN10289555). Terthiophenes and polyynes from Asteraceae species have been suggested as components in plant-derived compositions for treating herpes and cold sores (International (PCT) Application Publication No. WO2015/034665).

International (PCT) Application Publication No. WO2014/006626 discloses the use of *A. graveolens* extract, among extracts of other plants, as pest repellent.

There is an ongoing attempt to develop plant-based compositions for treating skin disorders and damages. For example, U.S. Patent Application Publication No. 2007/0122492 discloses plant extracts and dermatological formulations comprising one or more plant extracts that are capable of inhibiting extracellular proteases. Also disclosed is the use of the plant extracts as dermatological agents suitable for treating or preventing various dermatological conditions, including wrinkling or sagging of the skin, irradiation induced skin and/or hair damage, deepening of skin lines, elastotic changes in the skin, as well as for the routine care of the skin, hair and/or nails.

U.S. Pat. No. 8,771,758 discloses a method of improving the aesthetic appearance of aging skin by topically applying a composition comprising a *Tiliacora triandra* Diels plant extract capable of inhibiting collagenase activity.

It is highly desirable and it would be advantageous to have improved compositions and methods effective in protecting tissues comprising epithelial cells in general and skin in particular from deleterious effects caused by environmental hazards, particularly by pollutants.

SUMMARY OF THE INVENTION

The present invention provides extracts of *Asteriscus graveolens* plant and compositions comprising same useful in protecting mammalian tissues from pollution. The extracts and compositions of the invention are highly useful in preventing a damage caused to tissues comprising epithelial cells by exposure to various pollutants, particularly chemical substances including chemicals found in smoke (e.g. engine smoke, tobacco smoke and fire smoke) and chemicals found in industrial waste.

The present invention is based in part on the unexpected discovery that a fraction of *Asteriscus graveolens* extract, soluble in a polar solvent, is useful in protecting against toxic challenges met by the skin and other epithelial-cell comprising tissues that come in contact with exogenous pollutant, for example lung tissue. The extract fraction thereby improved the skin appearance and vitality and reduced premature skin aging. The extracts of the present invention exhibit a significant protective effect on cell viability, increasing the cell survival following exposure to a smoke-tainted medium.

According to one aspect, the present invention provides a method for protecting a tissue comprising epithelial cells from the deleterious effect of at least one pollutant comprising administering to a subject in need thereof a polar solvent extract derived from *Asteriscus graveolens* plant and/or a fraction thereof or a composition comprising same, thereby protecting said tissue from the at least one pollutant.

According to certain embodiments, the subject has been exposed, and/or is exposed and/or is expected to be exposed to the at least one pollutant. Each possibility represents a separate embodiment of the present invention.

According to certain embodiments, the at least one pollutant originates from at least one of combustion gas, industrial pollutions and smoke. According to certain embodiments, the pollutant is smoke-associated pollutant. According to certain exemplary embodiments, the pollutant originates from tobacco smoke.

According to certain embodiments, the subject has been exposed, and/or is exposed and/or is expected to be exposed to smoke. According to some embodiments, the smoke is tobacco smoke. According to other embodiments, the subject is a tobacco smoker or is exposed to tobacco smoke (secondary or passive smoker).

According to certain embodiments, the subject is exposed to the at least one pollutant sporadically. According to other embodiments, the subject is exposed to the at least one pollutant on a daily basis.

According to some embodiments, protecting the tissue from the deleterious effect of the at least one pollutant results in at least one outcome selected from the group consisting of increased viability of the tissue cells, improved health of the tissue cells and reduced premature aging of the tissue cells. Each possibility represents a separate embodiment of the invention. According to certain exemplary embodiments, the tissue cells are epithelial cells. According to certain embodiments, protecting the tissue comprises increasing the tolerance of said tissue cells to the at least one pollutant. According to certain exemplary embodiments, protecting the tissue comprises increasing the tolerance of the tissue epithelial cells to the at least one pollutant.

Without wishing to be bound by any specific theory or mechanism of action, the extract of the present invention is effective in increasing the tolerance of the epithelial-cell comprising tissue to the pollutants by decreasing the epithelial cells response or sensitivity to said pollutants.

According to certain embodiments, the method of the present invention is for protecting a tissue selected from the group consisting of skin, nasal cavity, oral cavity, pharynx, larynx, trachea and/or lung tissue. Each possibility represents a separate embodiment of the invention.

According to certain exemplary embodiments, the epithelial tissue forms part of the skin. According to these embodiments, the method comprises topically administering the polar solvent extract derived from *A. graveolens* and/or a fraction thereof or a composition comprising same to the skin of the subject in need thereof. According to further embodiments, protecting skin from the deleterious effect of the at least one pollutant results in at least one outcome selected from the group consisting of increased skin cell viability, improved skin appearance, and/or reduced premature skin aging. Each possibility represents a separate embodiment of the present invention. According to certain embodiments, improved skin appearance and/or reducing premature skin aging comprises reduction in the appearance of at least one of skin wrinkles, skin brown spots and skin red spots. According to some embodiments, improving skin appearance and/or reducing premature skin aging comprises maintaining and/or improving the skin hydration value as compared to a pre-determined threshold value.

According to certain embodiments, the skin hydration pre-determined threshold value is obtained from a skin area of the same subject not exposed to the at least one pollutant. According to other embodiments, the skin hydration pre-determined threshold value is obtained from a skin area of a subject not exposed to the at least one pollutant.

According to additional exemplary embodiments, the epithelial tissue forms part of at least one of the lung, trachea and nasal cavity. According to certain embodiments, the method comprises administering the polar solvent extract, and/or fraction thereof or a composition comprising same via inhalation. Additionally or alternatively, the method comprises administering the polar solvent extract, and/or a fraction thereof or a composition comprising same by nozzle spray.

According to yet additional embodiments, the epithelial tissue forms part of at least one of pharynx and larynx. According to these embodiments, the polar solvent extract, and/or a fraction thereof or a composition comprising same is formulated for oral care.

The concentration of the *A. graveolens* extract/and or fraction thereof to be administered to the subject and the administration regimen depends, inter alia, on the tissue type to be treated, the severity of exposure and the severity of symptoms caused by the at least one pollutant. According to certain embodiments, a composition comprising the polar solvent extract and/or a fraction thereof at a concentration of from 0.1% to 10% (w/w) is administered. According to other embodiments, the composition comprises from 0.2% to 5.0% of the polar solvent extract and/or fraction thereof. According to certain exemplary embodiments, a composition comprising 1% of the polar solvent extract and/or fraction thereof is administered.

According to certain embodiments, the extract, fraction thereof or a composition comprising same is administered at least once daily. According to certain exemplary embodiments, the extract, fraction thereof or a composition comprising same is administered twice daily. According to some embodiments, the extract, fraction thereof or a composition comprising same is administered for at least a week, for at least two weeks, for at least three week or for at least 4 weeks. Each possibility represents a separate embodiment of the present invention. According to certain exemplary embodiments, the extract, fraction thereof or composition comprising same is administered during four weeks.

According to some embodiments, the pollutant comes in contact with the tissue comprising epithelial cells in its isolated form. According to other embodiments, the pollutant is present in a medium coming in contact with the subject tissue.

According to certain embodiments, the pollutant and/or the medium comprising same comes in contact with the skin of the subject. According to other embodiments, the pollutant and/or the medium comprising same comes in contact with the oral cavity of the subject. According to additional embodiments, the pollutant and/or the medium comprising same comes in contact with the respiratory system of the subject.

According to certain embodiments, the pollutant is present in a medium selected from the group consisting of ambient air, water and soil.

According to some embodiments, the subject is human. According to certain exemplary embodiments, the human subject is a smoker.

According to certain embodiments, the compositions and methods of the present invention employs a fraction of the polar solvent extract. According to other embodiments, the compositions and methods of the present invention employs the complete polar solvent extract derived form *A. graveolens*.

According to some embodiments, the polar solvent extract and/or the fraction thereof is derived from any of the aerial parts of the *Asteriscus graveolens* plant. According to further embodiments, the aerial part is selected from the group consisting of a stem, a leaf, a seed, a flower, a fruit and any combination thereof. According to certain embodiments, the aerial part is a stem and/or a leaf. Each possibility represents a separate embodiment of the present invention.

According to some embodiments, the polar solvent is water. According to other embodiments, the polar solvent comprises water and at least one additional polar solvent. According to certain embodiments, the additional polar solvent is selected from the group consisting of 1,2,3-trihydroxypropane (also known as glycerin or glycerol), ethanol, propylene glycol, butylene glycol, methanol, and acetone. Each possibility represents a separate embodiment of the present invention. In some embodiments, the polar solvent comprises water and glycerin. In other embodiments, the polar solvent comprises water and butylenes glycol. In yet other embodiments, the polar solvent comprises propylene glycol. According to certain exemplary embodiments, the extract or the fraction thereof is in a form of a solution comprising water and glycerin, wherein the glycerin concentration ranges from 40% to 60% (w/w) relative to the total weight of the solution.

According to certain typical embodiments the solution comprises 50% glycerin (w/w).

According to certain embodiments, the solution comprising the extract and/or fraction thereof according to the present invention and glycerin is in a form of a clear, homogenous solution. According to some exemplary embodiments, the solution is stable for at least three months at a temperature of 40-50° C. without the formation of visible aggregates.

According to certain embodiments, the extract or the fraction thereof is essentially devoid of essential oils. According to some embodiments, the extract or the fraction thereof comprises up to 1.0%, 0.5%, 0.1%, 0.05%, 0.03%, 0.01%, 0.005%, or 0.001% w/w of essential oils. Each possibility represents a separate embodiment of the invention. According to further embodiments, the extract or the fraction thereof is devoid of essential oils.

According to certain embodiments, the extract or the fraction thereof is essentially devoid of oils.

According to additional aspect, the present invention provides a composition comprising a polar solvent extract derived from *Asteriscus graveolens* plant or a fraction thereof in an amount effective in protecting a tissue comprising epithelial cells from the deleterious effect of at least one pollutant, further comprising a cosmetically, and/or pharmaceutically acceptable and/or a dermatological diluents, excipient or carrier.

According to some embodiments, the extract or the fraction thereof is derived from any of the aerial parts of the *Asteriscus graveolens* plant. According to further embodiments, the aerial part is selected from the group consisting of stem, leaf, seed, flower, fruit and any combination thereof. According to certain embodiments, the aerial part is a stem and/or a leaf. Each possibility represents a separate embodiment of the present invention.

According to certain embodiments, the extract or the fraction thereof is essentially devoid of essential oils. According to some embodiments, the extract fraction comprises up to 1%, 0.5%, 0.1%, 0.05%, 0.03%, 0.01%, 0.005%, or 0.001% w/w of essential oils. Each possibility represents a separate embodiment of the invention. According to further embodiments, the extract or the fraction thereof is devoid of essential oils.

According to certain embodiments, the extract or the fraction thereof is essentially devoid of oils.

According to certain embodiments, the composition comprises the *Asteriscus* extract and/or the fraction thereof at a concentration of 0.1% to 10% (w/w) relative to the total weight of the composition. According to other embodiments, the composition comprises the extract or the fraction thereof at a concentration of 0.2% to 5%. According to certain exemplary embodiments, the composition comprises the extract and/or the fraction thereof at a concentration of 1% (w/w) relative to the total weight of the composition.

According to some embodiments, the composition further comprises at least one additional plant extract. According to other embodiments, the composition further comprises at least one microalgae extract.

According to some embodiments, the composition further comprises an additional active agent selected from the group consisting of an anti-oxidant, a chelator, a cleansing agent, a skin protectant, a sunscreen, a skin lightening agent, an anti-wrinkling agent, an anti-inflammatory agent, anti-aging agent, and any combination thereof. Each possibility represents a separate embodiment of the present invention.

According to some embodiments, the composition is formulated in a form selected from the group consisting of aqueous solution, cream, lotion, water in oil emulsion, oil in water emulsion, microemulsion, nanoemulsion, gel, serum and milk. Each possibility represents a separate embodiment of the present invention.

According to certain embodiments, the composition is formulated for topical administration. Any topical formulation as is known in the art can be used according to the teachings of the present invention.

According to certain embodiments, the composition is a cosmetic or dermatological composition further comprising a cosmetically acceptable or dermatological carrier, diluent and/or excipient.

According to some embodiments, the cosmetically acceptable or dermatological carrier is selected from the group consisting of a liposome, a micelle structure, a microcapsule, and any combination thereof. Each possibility represents a separate embodiment of the present invention.

According to some embodiments, the cosmetic composition further comprises a cosmetically acceptable or a dermatological additive. According to certain embodiments, the additive is selected from the group consisting of: fats, emulsifiers, co-emulsifiers, hydrophilic gelling agents, lipophilic gelling agents, preservatives, solvents, fragrances, fillers, hydrophilic filters, lipophilic filters, dyestuffs, pigments, neutralizers, pH buffers, penetration-enhancing agents, emollients, polymers and any combination thereof. Each possibility represents a separate embodiment of the present invention.

According to other embodiments, the composition is formulated for administration via a spray nozzle.

According to some embodiments, the composition is an inhalation composition. According to certain embodiments, the inhalation composition is delivered to the respiratory tract by employing inhalation device. According to certain embodiments, the inhalation device is selected form the group consisting of inhalers and nebulizers. Each possibility represents a separate embodiment of the invention. According to certain embodiments, the inhalation composition is administered by humidifier. According to other embodiments, the inhalation composition is administered through an air filtration system.

According to some embodiments, the composition is an oral care composition. According to certain embodiments, the oral care composition is in a form selected from the group consisting of toothpaste, dental cream, gel, powder, mouth wash, breath freshener, gingival massage cream, gargling tablet, lozenge and chewing gum. Each possibility represents a separate embodiment of the present invention. According to certain embodiments, the oral care composition comprises additional agent selected from the group consisting of white colorants, whitening agents, enzymes, anti-plaque agents, anti-staining agents, anti-microbial agents, anti-caries agents, flavoring agents, coolants, and salivating agents. According to some embodiments, the oral care composition further comprises a reagent selected from the group consisting of abrasives, surfactants, chelating agents, fluoride sources, thickening agents, buffering agents, solvents, humectants, carriers, and bulking agents. Each possibility represents a separate embodiment of the present invention.

According to additional embodiments, the compositions of the invention are directed for use in protecting a tissue comprising epithelial cell from the deleterious effects of a pollutant. According to certain embodiments, the tissue is selected from the group consisting of skin, nasal cavity, oral cavity, pharynx, larynx, trachea and/or lung tissue. Each possibility represents a separate embodiment of the invention.

According to additional aspect, the present invention provides a composition for use in protecting a tissue comprising epithelial cell from the deleterious effects of at least one pollutant, wherein the composition comprises a polar solvent extract derived from *Asteriscus* plant or a fraction thereof.

The extract derived from the *Asteriscus* plant, a fraction thereof and a composition comprising same are as described hereinabove.

Other objects, features and advantages of the present invention will become clear from the following description and examples.

DETAILED DESCRIPTION OF THE INVENTION

Figure 1A:
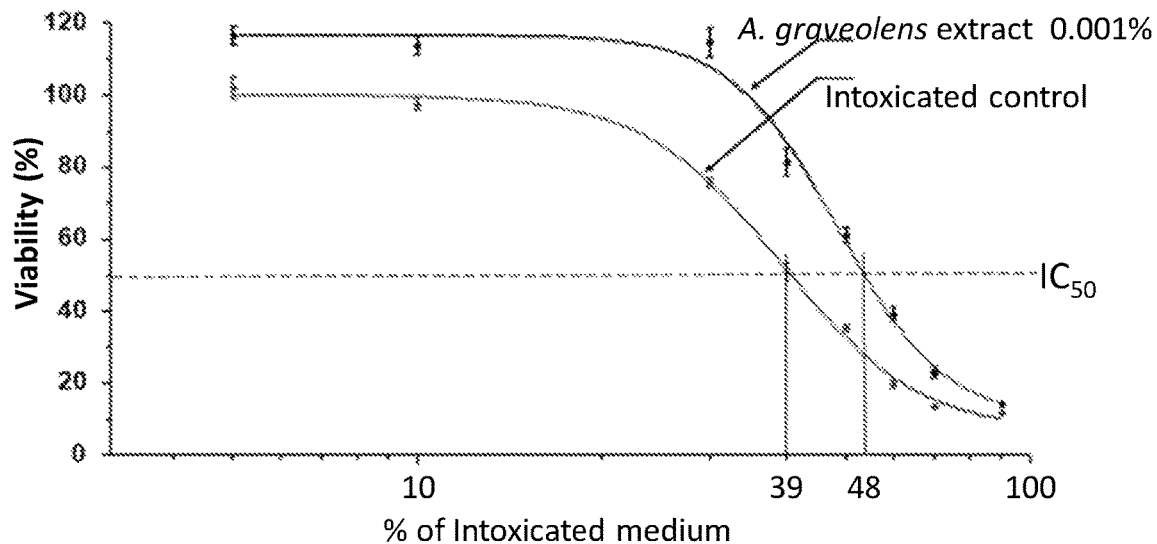
FIG. 1 provides graphic representations of the effect of *A. graveolens* extract on the viability of keratinocyte cells intoxicated with cigarette smoke. The effect of the extract was tested at concentrations of 0.001% (FIG. 1A) and 0.002% (FIG. 1B).

The present invention provides an extract derived from *Asteriscus graveolens* and/or fractions thereof and/or compositions comprising same for preventing and/or treating damage caused by pollutants to a tissue comprising epithelial cells.

The present invention is based in part on the unexpected discovery that a polar solvent extract of *A. graveolens* protected cultured human epithelial cells (epidermal and lung cells) from death and DNA damage induced by cigarette smoke tainted medium. When applied to skin exposed to smoke in vivo (by topical application to the skin of heavy smoker subjects) the extract had positive effect on the skin, reducing wrinkle counts and volume and improving skin tone, texture and hydration.

Without wishing to be bound by any particular theory or mechanism of action the high efficacy of the extract and compositions of the present invention in protecting and/or increasing tolerance of epithelial cells to damages caused by pollutants, particularly smoke-related pollutants, may be attributed to its ability to affect gene expression, particularly to reduce the expression of genes encoding for proteins involved in the processes of inflammation, oxidation and cell death and increase expression of at least one gene encoding a protein involved in toxin metabolism. The active contribution of the extract to the cell protective mechanism may be attributed to particular components present within the *Asteriscus graveolens* plant that are soluble in polar solvents and/or to the extracting methods that preserve the plant-component protective qualities.

The extracts and compositions of the invention are highly useful in preventing damage caused by various pollutants to epithelial tissues. The extracts and compositions of the invention are further useful in preventing air pollution damages such as those caused by fire smoke, engine combustion gas and industrial pollution. One example for air pollution source is tobacco smoke. Numerous studies have shown the connection between toxins found in cigarette smoke and damages to the epithelial cells of lungs and skin. Cigarette smoke contains over 4,700 chemical compounds of which about 60 are widely recognized as carcinogenic. Cigarette smoke can thus serve as a broad model of airborne pollution.

Definitions

The terms "polar solvent extract" and "polar solvent extract derived from *Asteriscus* plant" and "an extract derived from *Asteriscus* plant wherein the extract is soluble in a polar solvent" are used herein interchangeably and refer to an extract obtained by extracting any aerial part of *Asteriscus graveolens* with a polar solvent. The term "fraction thereof" refers to at least one fraction of the extract. According to certain exemplary embodiments, the fraction is obtained by filtering source crude extract.

The term "deleterious effect" or its plurality "deleterious effects" with reference to the at least one pollutant refers to any harm caused to a tissue comprising epithelial cells, particularly a tissue lining both the outer surface (skin) and the inside cavities and lumen of the mammalian body. The deleterious effect may include, without limiting, loss of vitality, metabolism disorder, premature aging and/or cell death. The term "deleterious effect on skin" as used herein refers to any harm caused to the skin by pollutants as disclosed in the invention, including, without limiting, premature skin aging, loss of vitality, and deterioration in the appearance of the skin, particularly the formation of wrinkles.

The term "skin damage" as used herein refers to harm to any of the skin layers as a result of exposure to pollutants as described in the invention. The term "pollutant" as used herein refers to a compound introduced into the environment that has undesired effects, or that adversely affects the characteristic and function of the medium to which it has been introduced. As used herein the term "pollutant" mainly refers to a xeno chemical compound that is poisonous and/or harmful to a mammal. According to certain embodiments, the pollutant is a smoke-related substance, particularly a smoke-related substance that damages epithelial cells. According to certain exemplary embodiments, the smoke is tobacco smoke.

The term "smoker" is used herein in its broadest scope and refers to a subject smoking cigarettes, pipes and any other commonly used smoking material.

As used herein, the term "secondary or passive smoker" refers to a subject exposed to tobacco smoke produced by a smoker.

The terms "epithelium", "epithelial tissues", and "epithelial cells" are used herein interchangeably and are meant to refer to the membranous tissue composed of one or more layers of cells separated by very little intercellular substance and forming the covering of most internal and external surfaces of the body and its organs. The term explicitly includes viable keratinocytes. The term "tissue comprising epithelial cells" refers to a tissue comprising epithelial cells as part of its structure. The epithelial cells according to the invention are found inter alia in the skin, oral and nasal cavities, pharynx, larynx, esophagus, trachea and lungs.

As used herein the term "essential oil" refers to volatile oil derived from leaves, stems, flowers or twigs of *Asteriscus graveolens*. Essential oils are hydrophobic oils derived from plant matter and substantially devoid of lipids or lipid oils.

The terms "essentially devoid of oil" and "essentially devoid of essential oil" are used herein in reference to the extract of the present invention to define an extract or a fraction thereof comprising oil or essential oil in an amount below the detectable level by a method common in the art. According to certain embodiments, the polar solvent extract of the invention or a fraction thereof comprises less than 1% oil or less than 1% essential oil. According to certain additional embodiments, the polar solvent extract of the invention or the fraction thereof comprises less than 0.1% oil or less than 0.1% essential oil.

As used herein, the term "and/or" includes any and all combinations of one or more of the associated listed items. Each possibility represents a separate embodiment of the invention.

According to one aspect, the present invention provides a method for protecting a tissue comprising epithelial cells from the deleterious effect of at least one pollutant, comprising administering to a subject in need thereof a polar solvent extract derived from *Asteriscus graveolens* plant or a fraction thereof, or a composition comprising same, thereby protecting said tissue from the deleterious effect of the at least one pollutant.

According to certain embodiments, the subject is a mammal. According to certain exemplary embodiments, the subject is a human.

*Asteriscus graveolens* belongs to the Asteraceae family and grow in hot and dry environments. The plant essential oils are known in the traditional medicine for being stomachic, for treating fever, gastrointestinal tract complaints, cephalic pains, and bronchitis, and as an anti-inflammatory agent. The use of the plant for its antimicrobial and hypoglycemic properties has also been described (Cristofari et al., 2012, ibid). While such uses of Asteraceae were known, *Asteriscus graveolens* extract had not been assigned an International Nomenclature of Cosmetic Ingredients (INCI) name and it was not registered in the Personal Care product Council (US) and/or the Inventory of Existing Cosmetic Ingredients in China before the present invention. Unexpectedly, the present invention now discloses that a polar solvent extract of *Asteriscus graveolens* substantially devoid of essential oils, is useful in protecting, and/or treating and/or preventing pollution-related epithelium damages, such as skin damages.

The extracts of the present invention may be obtained from *A. graveolens* plants grown in its natural habitat or from plants grown under designated agricultural conditions. Any variety of the plant can be used.

The extract may be obtained from any part of the plant. According to some embodiments, the extract is derived from any of the aerial parts of the *Asteriscus graveolens* plant. According to further embodiments, the aerial part is selected form the group consisting of stems, leaves, seeds, fruit and any combination thereof. According to certain embodiments, the aerial part is a stem or a leaf. Any possibility represents a separate embodiment of the invention.

According to some embodiments, the extract derived from *Asteriscus graveolens* or a fraction thereof comprises 50% by volume less essential oil as compared to percent of essential oil in *Asteriscus graveolens* aerial parts. According to certain embodiments, the extract derived from *Asteriscus graveolens* or a fraction thereof comprises 60% by volume less essential oil as compared to percent of essential oil in *Asteriscus graveolens* aerial parts. According to certain embodiments, the extract derived from *Asteriscus graveolens* or a fraction thereof comprises 70% by volume less essential oil as compared to percent of essential oil in *Asteriscus graveolens* aerial parts. According to certain embodiments, the extract derived from *Asteriscus graveolens* or a fraction thereof comprises 80% by volume less essential oil as compared to percent of essential oil in *Asteriscus graveolens* aerial parts. According to certain embodiments, the extract derived from *Asteriscus graveolens* or a fraction thereof comprises 90% by volume less essential oil as compared to percent of essential oil in *Asteriscus graveolens* aerial parts. According to certain embodiments, the extract derived from *Asteriscus graveolens* or a fraction thereof comprises 95% by volume less essential oil as compared to percent of essential oil in *Asteriscus graveolens* aerial parts. According to certain embodiments, the extract derived from *Asteriscus graveolens* or a fraction thereof comprises 99% by volume less essential oil as compared to percent of essential oil in *Asteriscus graveolens* aerial parts. According to certain embodiments, the extract derived from *Asteriscus graveolens* or a fraction comprises 99.9% by volume less essential oil as compared to percent of essential oil in *Asteriscus graveolens* aerial parts.

According to some embodiments, the extract derived from *Asteriscus* or a fraction thereof is devoid of 6-oxocyclonerolidol. According to certain embodiments, the extracts of the invention comprises less than 0.7%, 0.5%, 0.2%, 0.1%, 0.05%, or 0.01% 6-oxocyclonerolidol. Each possibility represents a separate embodiment of the invention. According to some embodiments, the extract derived from *Asteriscus* or a fraction thereof is devoid of 6-hydroxycyclonerolidol. According to other embodiments, the extract derived from *Asteriscus* or a fraction thereof is devoid of cis-8-acetoxychrysanthenyl acetate.

Various polar solvents as are known in the art can be used to obtain the extracts of the present invention. According to certain exemplary embodiments, the polar solvent comprises water and at least one additional polar solvent selected from the group consisting of 1,2,3-trihydroxypropane (also known as glycerin or glycerol), ethanol, propylene glycol, butylene glycol, methanol, and acetone. Each possibility represents a separate embodiment of the present invention.

According to certain exemplary embodiments, the pollutant-protecting components are extracted from the *A. graveolens* plant parts using water as the polar solvent, with glycerin (1,2,3-trihydroxypropane) added to the aqueous medium after obtaining the desired extract fraction. According to these embodiments, the present invention provides an extract solution comprising at least one fraction of water extract of *A. graveolens* and glycerin. According to some embodiments, the ratio of the at least one fraction of water extract of *A. graveolens* to glycerin is from 1:3 to 3:1. According to certain currently exemplary embodiments, the ratio is 1:1. This extract solution is clear, translucent, homogenous and highly stable for at least three month even when kept under elevated temperature of 40-50° C. without the formation of visible aggregates.

According to some embodiments, the pollutant comes in contact with the tissue comprising epithelial cells in its isolated form. According to other embodiments, the pollutant is present in a medium coming in contact with the subject tissue.

As used herein, the term "pollution" refers to a medium comprising at least one pollutant.

Urban air pollution, caused by industry, vehicle fumes, tobacco smoke and other sources is known to have a detrimental effect on human skin and causes early aging and wrinkles (Drakaki E et al., 2014. Frontiers in Environmental Science 2:1-6). Pollution and smog are composed of a highly complex mixture of molecules and particles that are breathed in and absorbed through, inter alia, the skin. The composition of pollution may vary significantly, but typically contains several main categories of compounds (Ghelfi E. 2011. In: Advanced Topics in Environmental Health and Air Pollution Case Studies. Anca Maria Moldoveanu Ed. InTech. pp. 121-156).

Tobacco smoke (cigarette smoke being the most common type) is also considered a source of air pollution and comprises up to 4600 compounds and toxins known to be detrimental to human health. Cigarette smoking causes early aging and has visible and pronounced effects on skin (Ortiz A and Grando S A. 2012. Int J of Dermatol 51:250-262).

Pollutants may be categorized to one or more groups selected from volatile organic compounds (VOCs), polyaromatic hydrocarbon (PHAs), oxides and heavy metals.

VOCs are emitted to air from exhaust emissions and the use of organic solvents in paints and various industrial facilities. Examples of such compounds are aliphatic hydrocarbons, ethyl acetate, glycol ethers and acetone. Cigarette smoke emissions includes VOCs including benzene and associated monoaromatics, aldehydes and ketones, furans, acrylonitrile, 1,3-butadiene, vinyl chloride, and nitromethane, all known air pollutants (Sampson M M et al., 2014. Anal Chem. 86(14):7088-7095). Exposure of skin to VOCs may lead to an increase in cytokines which could in turn lead to inflammation, allergic reactions, atopic dermatitis or eczema.

PAHs compose a group of more than 100 different chemicals that are released from burning coal, oil, gasoline, trash, tobacco, wood, or other organic substances such as charcoal-broiled meat. They are also called polynuclear aromatic hydrocarbons. These cyclic molecules have been implicated in the development of skin cancer. When activated, they form diols and epoxides which can penetrate the skin and bind to the cell DNA, leading to carcinogenesis. It has been also noted that for some chemicals (for example benzo[a]pyrene), the effect was enhanced with exposure to UVA. Cigarette smoke is also known to contain PAHs including (among others) 1-methylanthracene (1-MA), phenanthrene (PA), and benzo[a]pyrene (Lee L L et al., 2002. Bone 30(6):917-923; Siddens L K et al., 2012. Toxicol Appl Pharmacol 264(3):377-386; Tithof P K et al., 2002. FASEB J. 16(11): 1463-4).

Oxides, such as sulfur dioxide, nitrogen dioxide and carbon monoxide form another group of molecules known to exist both in air pollution and in cigarette smoke. NOx and CO have been associated with atopic and flexural eczema and atopic dermatitis (Drakaki, 2014, ibid).

Reactive oxygen species (ROS) and free radicals associated with ROS are associated with oxidative stress and lipid peroxidation. These have been shown to lead to transepidermal water loss, degeneration of connective tissue in the skin and an increase in MMPs (metalloproteinases)-enzymes which break down connective skin tissue (Jorgensen L N K et al., 1998. Surgery 123:450-455). Free radicals released by cigarette smoke have also been shown to lead to DNA damage (Albino A P et al., 2006. Int J Oncol 28:1491-1505). Reactive oxygen species are found both in cigarette smoke and in air pollution. As an example of its deleterious effects, an acute rise in blood carboxyhaemoglobin from 1.7% to 5.1% has been measured in subjects in New York City after 30 min of exercise near busy roadway (Nicholson J P. 1983. Physician Sportsmed 11: 135-138).

Traces of heavy metals are also found in both air pollution and cigarette smoke including cadmium, lead, nickel, and chromium. Exposure to trace levels of heavy metals has not been shown to affect skin quality, but accumulation of heavy metals over time has been shown to be associated with higher risks of cancer.

An additional and important class of pollutants is particulate matter (PM). This class of pollutants is not defined by its composition but rather by its size; particulate matter is often divided into three main groups: the coarse fraction, containing the larger particles with a size range of from 2.5 to 10 µm (PM10-PM2.5); the fine fraction containing a smaller size range of up to 2.5 µm (PM2.5); and the particles in the fine fraction which are smaller than 0.1 µm and are called ultrafine particles.

Most of the total mass of airborne particulate matter is usually made up of fine particles ranging from 0.1 to 2.5 µm. Ultrafine particles often contribute only a few percent to the total mass of airborne pollutant, although encompass over 90% of the particles number.

Numerous studies have shown that cigarette smoke emits PM2.5 similar to exhaust fumes (Invernizzi G et al., 2004. Tob Control 13:219-221) and that these particles have a detrimental effect on human health, particularly on skin health. Correlations have been found between exposure to PM pollution and signs of skin aging including pigment spots, nasolabial folds, and wrinkles (Vierkötter A et al., 2010. J Investigative Dermatol 130:2719-2726).

In some embodiments, the pollution is air pollution. In some embodiments, the air pollution is smoke. In other embodiments the air pollution is tobacco smoke.

Many of the compounds found in cigarette smoke are also found in air-polluted cities and industrial areas. Hence, the composition of cigarette smoke is a representative example of the composition of air pollution.

According to certain exemplary embodiments, the pollutant is selected from the group consisting of pollutants presented in Table 1.

TABLE 1

Primary toxic and carcinogenic components of cigarette smoke including vapor-phase and particulate phase components

| Agent | Category | Toxic | Ciliotoxic | Carcinogenic | Co-carcinogenic/Promoter |
|---|---|---|---|---|---|
| Carbon Monoxide | Oxide | x | | | |
| Nitrogen Oxides ($NO_x$) | Oxide | x | | | |
| Hydrogen Cyanide | VOC | x | x | | |
| Formaldehyde | VOC | | x | x | |
| Acrolein | VOC | | x | | |
| Acetaldehyde | VOC | | x | | |
| Ammonia | VOC | x | | | |
| Hydrazine | Leads to formation of reactive oxygen species | | | x | |
| Vinyl Chloride | VOC | | | x | |
| Urethane | VOC | | | x | |
| 2-Nitropropane | VOC | | | x | |
| Quinoline | PAH | | | x | |
| Benzo[a]pyrene | PAH | | | x | x |
| Dibenz[a,h]anthracene | PAH | | | x | x |
| Benzo[b]fluoranthene | PAH | | | x | x |
| Benzo[j]fluoranthene | PAH | | | x | x |
| Dibenzo[a,h]pyrene | PAH | | | x | x |
| Dibenzo[a,i]pyrene | PAH | | | x | x |
| Dibenz[a,j]acridine | PAH | | | x | x |
| Indeno[1,2,3-cd]pyrene | PAH | | | x | x |
| Benzo[c]phenanthrene | PAH | | | x | x |
| Benz[a]anthracene | PAH | | | x | x |
| Benzo[e]pyrene | PAH | | | x | x |
| Chrysene | PAH | | | x | x |
| Methylchrysene | PAH | | | x | x |
| Mehtylfluoranthene | PAH | | | x | x |
| Dibenz[a,c]anthracene | PAH | | | x | x |
| Dibenz[a,h]acridine | PAH | | | x | x |
| Dibenzo[c,g]carbazole | PAH | | | x | x |
| Mehtylnaphtalenes | PAH | | | | x |
| 1-Methylindoles | VOC | | | | x |
| Dichlorostilbene | PAH | | | | x |
| Catechol | PAH | | | | x |
| 3-Methycatechol | PAH | | | | x |
| 4-Methycatechol | PAH | | | | x |
| 4-Ethycatechol | PAH | | | | x |
| 4-n-Propylcatechol | PAH | | | | x |
| Nitrosodimethylamine | VOC | | | x | |
| Nitrosoethymethylamine | VOC | | | x | |
| Nitrosodiethylamine | VOC | | | x | |
| Nitrosodi-n-propylamine | VOC | | | x | |
| Nitrosodi-n-butylamine | VOC | | | x | |
| Nitrosopyrrolidine | VOC | | | x | |
| Nitrosopiperidine | VOC | | | x | |
| Nitrosomorpholine | VOC | | | x | |
| N'-Nitrosonornicotine | VOC | | | x | |
| 4-(methylnitrosamino)-1-(3-pyridyl)-1-butanone | VOC | | | x | |
| N'-Nitrosoanabasine | VOC | | | x | |
| N'-Nitrosoanatabine | VOC | | | x | |
| Aromatic Amines | PAH | | | x | |
| Aromatic Nitrohydrocarbons | PAH | | | x | |
| Nickel | Heavy metal | | | x | |
| Arsenic | Heavy metal | | | x | |
| Cadmium | Heavy metal | | | x | |

The present invention now shows that polar solvent extracts of *A. graveolens* are highly effective in protecting epithelial cells from deleterious effects and/or damages caused by pollutants, particularly smoke-associated pollutants. The extracts and compositions comprising same are thus useful in protecting subjects, particularly human subject inclined to be exposed to pollution, particularly smoke related pollution.

According to certain embodiments, the human subject is exposed to tobacco smoke. According to certain exemplary embodiments, the human subject is a heavy smoker.

The dosage of the extract or the fraction thereof and the route of administration depend on the target tissue to be protected, the degree of exposure to pollutant and on characteristics of the subject, including gender, age and general health conditions, as is known to the skilled in the art. According to certain exemplary embodiments, the effective dose of the *A. graveolens* extract or fraction thereof is from 0.1% to 10%, 0.2% to 5% or about 1% (w/w relative to the total weight of the composition comprising same).

According to certain exemplary embodiments, the extract, fraction thereof or a composition comprising same is to be administered topically to a tissue selected from the group consisting of skin tissue, tracheal tissue, lung tissue and tissues within the oral cavity, the pharynx and the larynx.

According to certain embodiments, the extract, fraction thereof or a composition comprising same is to be administered topically to the skin. As used herein, the term "topical administration to skin" includes administration onto the skin surface as well as into the skin layers. According to certain embodiments, administration is performed onto the skin and/or transdermally and/or subcutaneously.

The polar solvent extract of *A. graveolens* or a fraction thereof can be administered to a subject in need thereof per se, or in a composition comprising same.

According to additional aspect, the present invention provides a composition comprising a polar solvent extract derived from *Asteriscus* plant or a fraction thereof in an amount effective in protecting a tissue comprising epithelial cells from the deleterious effect of at least one pollutant, further comprising a cosmetically, pharmaceutically or dermatologically acceptable diluents, excipient or carrier.

As described hereinabove, the extract of the invention or a fraction thereof is intended for use in protecting epithelial cells within at least one of the skin, trachea, lung, the oral cavity, pharynx and larynx. Any composition known in the art to be suitable for applying an active ingredient to skin, trachea, lung, oral cavity, pharynx and larynx can be used according to the teachings of the invention, as long as the protecting activity of the extract of the invention against deleterious effect of pollution is kept.

According to some embodiments, the composition is selected from the group consisting of cosmetic composition, oral care composition, and inhalation composition. Each possibility represents a separate embodiment of the invention.

The term "cosmetic composition" refers to a composition suitable for topical application, particularly topical application onto skin in mammals. According to certain embodiments, the composition has a cosmetically beneficial effect upon the skin as described herein.

The term "composition for oral care" as used herein refers to a composition suitable for administration to the oral cavity and/or pharynx and/or larynx of an individual. The composition can be used as a mouth wash, toothpaste, breath freshener etc. as is known in the art.

The term "inhalation composition" as used herein, refers to a composition directed to the respiratory system. The inhalation composition is designed to reach epithelial cells in the respiratory system.

According to yet another aspect, the present invention provides a composition for use in protecting a tissue comprising epithelial cell from the deleterious effects of at least one pollutant, wherein the composition comprises a polar solvent extract derived from *Asteriscus* plant or a fraction thereof.

According to certain embodiments, the composition is a cosmetic composition.

According to other embodiments, the composition is an inhalation composition further comprising a therapeutically acceptable diluents, excipient or carrier.

According to additional embodiments, the composition is an oral care composition further comprising diluents, excipient or carrier suitable for oral care.

According to certain embodiments, the composition is to be administered topically to the tissue comprising epithelial cells. According to some embodiments, the tissue comprising epithelial cell is selected from the group consisting of skin, nasal cavity, oral cavity, pharynx, larynx, trachea and/or lung tissue. Each possibility represents a separate embodiment of the invention.

Cosmetic Compositions

The cosmetic compositions of the invention may comprise additional acceptable cosmetic agents as known in the art. According to some embodiments, the cosmetic agent is selected from the group consisting of: botanical extracts, peptides, oligonucletotides, oligo- or poly-saccharides, glycosides, alkaloids, flavonoids, polyphenols, terpenoids, polyketides, carotenoids, fatty acids or derivatives thereof, steroids, xanthines, retinoids, α-hydroxy acids, β-hydroxy acids, α-2 adrenergic inhibitors, β-adrenergic agonists, aromatase inhibitors, anti-estrogens, hydroquinone, ascorbic acid, kojic acid, corticosteroids, mucopolysaccharides, collagen, estrogens, isoflavonoids, cinnamic acid, benzoyl peroxide, tropolone, catechol, mercaptoamine, niacinamide, tocopherol, ferulic acid, azelaic acid, botulinum, urea, a derivative, salt thereof, and any combination thereof. Each possibility represents a separate embodiment of the invention.

According to some embodiments, the cosmetic composition further comprises a cosmetically acceptable diluent, carrier or excipient. According to further embodiments, the cosmetically acceptable carrier is selected from the group consisting of a liposome, a micelle structure, a microcapsule, and a combination thereof. Each possibility represents a separate embodiment of the invention.

According to some embodiments, the cosmetic composition further comprises an acceptable additive. According to certain embodiments, the additive is selected from the group consisting of: fats, emulsifiers, co-emulsifiers, hydrophilic gelling agents, lipophilic gelling agents, preservatives, solvents, fragrances, fillers, hydrophilic filters, lipophilic filters, dyestuffs, neutralizers, penetration-enhancing agents, polymers and any combination thereof. Each possibility represents a separate embodiment of the present invention.

The quantities of the various additives are those conventionally used in cosmetic and dermatological preparations as is known to a person skilled in the art.

Non-limiting examples of suitable fats include mineral oils, oils of animal origin (lanolin), synthetic oils (isopropyl myristate, octyldodecyl, isostearyl isostearate, decyl oleate or isopropyl palmitate), silicone oils (cyclomethicone or dimethicone) and fluorinated oils. Fatty alcohol, fatty acids, waxes and gums, notably silicone gums and elastomers can also be used as fats.

Non-limiting examples of suitable emulsifiers and co-emulsifiers include polyglycerol fatty acid esters, sucrose fatty acid esters, sorbitane fatty acid esters, oxyethylene sorbitan fatty acid esters, PEG fatty alcohol ethers, glycerol fatty acid esters, alkyl sulphates, alkyl ether sulphates, alkyl phosphates, alkyl polyglucosides and dimethicone copolyols.

Non-limiting examples of suitable hydrophilic gelling include carboxyvinyl polymers (carbomer), acrylic copolymers such as acrylate/alkylacrylate copolymers, polyacrylamids, polysaccharides such as xanthan gum, guar gum, natural gums such as cellulose gum and derivatives, clays and 2-acrylamido-2-methylpropane acid copolymers.

Non-limiting examples of suitable lipophilic gelling agents include modified clays such as bentones, fatty acid metal salts, hydrophobic silica and ethylcellulose.

Non-limiting examples of suitable fillers include talc, kaolin, mica, serecite, magnesium carbonate, aluminum silicate and organic powders such as nylon.

Non-limiting examples of suitable neutralizers include soda, triethanolamine, aminomethyl propanol and potassium hydroxide.

Non-limiting examples of suitable penetration enhancing agents include alcohols and glycols (ethanol and propylene glycol), ethoxydiglycol, alcohols and fatty acids (oleic acid), fatty acid esters and dimethyl isosorbide.

Non-limiting examples of preservatives include benzoic acid, its salts and esters, sorbic acid and its salts, parabens and their salts, triclosan, imidazolidinyl urea, phenoxyethanol, DMDM hydantoin, diazolidinyl urea and chlorphenesin.

Non-limiting examples of suitable solvents include water, ethanol, glycerin, propylene glycol, butylene glycol, phosphate buffer, saline and sorbitol.

According to some embodiment, the composition comprises a bubbling agent as an additive. A bubbling agent is an agent that emits carbon dioxide gas when contacting liquid with a purpose, for example, to burst a capsule or promote intimate contact of a capsule's content with the surrounding material outside of the capsule.

According to some embodiment, the composition comprises other additives such as Generally Recognized as Safe (GRAS). GRAS is a United States of America Food and Drug Administration (FDA) designation indicating that a chemical or substance added to food is considered safe, and therefore exempted from the usual Federal Food, Drug, and Cosmetic Act (FFDCA) food additive tolerance requirements. According to some embodiments, the food supplement acceptable excipients comprise excipients in powders and other oral powders, excipients in topical powders, excipients in liquids, excipients in ointments or a combination thereof.

Non-limiting examples of excipients in topical powders include zinc oxide, talc, starch, kaolin, borate powder, zinc stearate, magnesium stearate, magnesium carbonate, precipitated calcium carbonate, bismuth subgallate and potassium aluminum sulfate powder.

Non-limiting examples of excipients in liquids include water, glycerin, propylene glycol, sweet-taste syrup, ethanol, fatty oil, ethylene glycol, polyethylene glycol and sorbitol.

Non-limiting examples of excipients in ointments include hydrophobic or hydrophilic base (including oil-soluble base, water-soluble base and suspended base) prepared by mixing fat, fatty oil, lanoline, Vaseline, glycerin wax, Japan wax, paraffin, paraffin sulphate, resins, higher alcohols, plastics, glycols, water and surfactant.

The quantities of the various additives are those conventionally used in food supplement as is known to a person skilled in the art.

Inhalation Compositions

The inhalation composition may include any excipient as known in the art, For example, US Application No. 2014/0377355 discloses the use of a combination of two or more poloxamers as optional excipients. Suitable poloxamers may include poloxamer 188 and poloxamer 407. According to some embodiments, the micronized poloxamer composition may include a particle size ranging between about 30 μm and about 70 μm.

The inhalation composition may be obtained in powder form and may be used to fill capsules, which may be later employed for inhalation. According to some embodiments, inhalation composition in powder form may be dissolved employing suitable solvents, such as sterile solution of sodium chloride and water, to obtain inhalation composition in solution form. The inhalation composition of the invention in solution form may be delivered to the respiratory tract using suitable inhalation devices, such as metered-dose inhalers (MDIs), dry powder inhalers, aerosols, syringe, pipette, eyedropper, nebulizers, or any suitable inhalation delivery apparatus.

Oral Care Composition

Another embodiment of the present invention refers to an oral composition comprising the extract of the invention or a fraction thereof. Oral compositions are intended to be brought into contact with the oral cavity, for example in the form of toothpastes, dental gels, dental creams, mouth washes, sugar-free candies for sucking, oral sprays, dental floss or dental care chewing gums. That is why they are also considered to be dental compositions. The term does not encompass food products dedicated for nutrition.

The oral compositions typically comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling active compounds, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, chlorhexidine, cetylpyridinium chloride, aluminium lactate, potassium citrate, potassium nitrate, potassium chloride, strontium chloride, hydrogen peroxide, aromas, sodium bicarbonate and/or odour correctants.

Formulations or products according to the invention in the form of chewing gums or, in particular, dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. Nos. 4,518,615; 5,093,136; 5,266,336; 5,601,858 or 6,986,709. In addition, chewing gum bases comprise further constituents, such as, for example, sugars, sugar substitutes or sweet-tasting substances in particular those described in WO 2009/21558, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations or products according to the invention (in particular those which are in the form of an oral care formulation or product or in the form of a formulation) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

The concentration of the *A. graveolens* within a selected composition depends on the composition type and intended use. According to certain exemplary embodiments, the composition comprises the extract or the fraction thereof derived from *Asteriscus* plant at a concentration of 0.1% to 10% (w/w). According to other embodiments, the composition comprises the extract or the fraction thereof at a concentration of 0.2% to 5%. According to certain exemplary embodiments, the composition comprises the extract or the fraction thereof at a concentration of 1% (w/w) relative to the total weight of the composition.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Preparation of *Asteriscus graveolens* Extract

Dry *Asteriscus graveolens* plant parts (having a moisture content of 10% (w/w) or less) were added to water at 10:1 w/w to 1:10 w/w ratio (plant parts:water) at room temperature. Plants parts were typically dried in an oven with air circulation set to a temperature of 20-60° C. for 12-72 h. The mixture was heated for 0.5-6 hours at 20-100° C. and left to cool overnight. Solids were removed by centrifugation at 4500 rpm for 30 min. Next, the supernatant was collected and filtered through 1.2 micron filter, then through 0.45 micron filter and lastly though 0.22 micron filter. The filtrate was collected. To the filtrate, 50-60% Glycerin was added to form the final solution. The formed solution is clear and homogenous, having a pH at the range of 4.0-6.5. Dry weight is in the range of 20-60 mg/g, typically in the range of 30-45 mg/g. The resulting solution is taken as 100% *Asteriscus graveolens* extract fraction.

Example 2: Identification of *Asteriscus graveolens* Extract as a Protectant Against Smoke-Related Pollution Cigarette smoke was chosen as a model for pollution, being a relevant environmental contaminant with proven effects on health in general and skin health and appearance, containing many relevant toxic compounds, including volatile organic compounds (VOC's), polyaromaitc hydrocarbon (PHAs), oxides and heavy metals Specific example of pollutants known to be present in cigarette smoke and have deleterious effect on epithelial cells are formaldehyde and polyaromatic hydrocarbons.

Study Design:

Extract fractions of a number of plant candidates were prepared essentially as described hereinabove for *A. graveolens*. The extracts were pre-screened for cytotoxicity by MTT reduction assay. In brief, MTT ((3-(4, 5-dimethylthiazolyl-2)-2, 5-diphenyltetrazolium bromide), a pale yellow substrate, is cleaved by succinate dehydrogenase present in living cells to yield a dark blue water-insoluble formazan salt. The transformation is proportional to the enzyme activity. After cell dissociation and formazan crystal solubilization using DMSO, the topical density (OD) of the extract at 540 nm, proportional to the number of living cells and their metabolic activity, was recorded with a microplate reader (VERSAmax, Molecular Devices).

The results of the MTT test were used to set the concentration(s) of the various plant extracts suitable to be used in the screening assay for extracts capable of protecting epithelial cells from smoke cytotoxicity.

Smoke Cytotoxicity Assay:

Normal human epidermal keratinocytes (NHEK) were cultured in culture medium for 24 hours. The medium was then removed and replaced by assay medium containing the plant extract fractions (test compounds) or the solvent alone added to the assay medium for control (2% $H_2O$ or 0.008% DMSO). After 24 hours of pre-incubation, the medium was replaced by cigarette smoke-intoxicated medium containing the test compounds (assay medium); $H_2O$, $H_2O$-DMSO or no addition as controls. The experiment was performed using several concentrations of cigarette smoke-intoxicated assay medium (8 concentrations ranging from 5% to 90% of intoxicated medium). Cells were incubated with the smoke-intoxicated medium for 24 hours.

Cell viability after exposure to the smoke-tainted medium was measured by photometry (MTT reduction as described above). The cytotoxicity of increasing concentrations of smoke-tainted medium (increasing toxic insult) was plotted, and the $IC_{50}$ of the smoke-tainted medium was determined (percentage of smoke tainted medium resulting in 50% inhibition of cell viability). This serves as the key measure in this assay: an increase in the $IC_{50}$ (representing an increase in the dose of tainted medium necessary to have a significant toxic effect, i.e. a decrease in said medium's toxicity) represents a protective effect of the plant extract fraction.

Experiments were conducted in triplicate (except for non-intoxicated control where n=6).

Various plant extracts were screened, wherein *Asteriscus graveolens* extract was highlighted as top lead. The experiments showed that extract fraction of *Asteriscus graveolens* exhibits marked protective effect against cigarette smoke intoxication. Cell death of 50% was observed at 33.1% smoke intoxicated medium ($IC_{50}$=33.1) while 0.01% of *A. graveolens* extract in the medium protected the cells up to 47.5% of intoxicated medium (an increase of about 43% in the $IC_{50}$).

The assay confirmed polar solvent extract of *Asteriscus graveolens* as a lead for protecting tissues comprising epithelial cells from a common and multi-ingredient toxin mixture such as cigarette smoke. The results show an increased vitality of cells treated with the extract as compared to untreated cells.

Example 3: Effect of Various Concentrations of *A. graveolens* Extract on Smoke-Challenged Skin Epithelial Cells The effect of several concentrations of *A. graveolens* extract produced as described in Example 1 hereinabove was examined. Cell viability assay was conducted as described in Example 2 hereinabove with the control medium being $H_2O$.

Figure 1B:
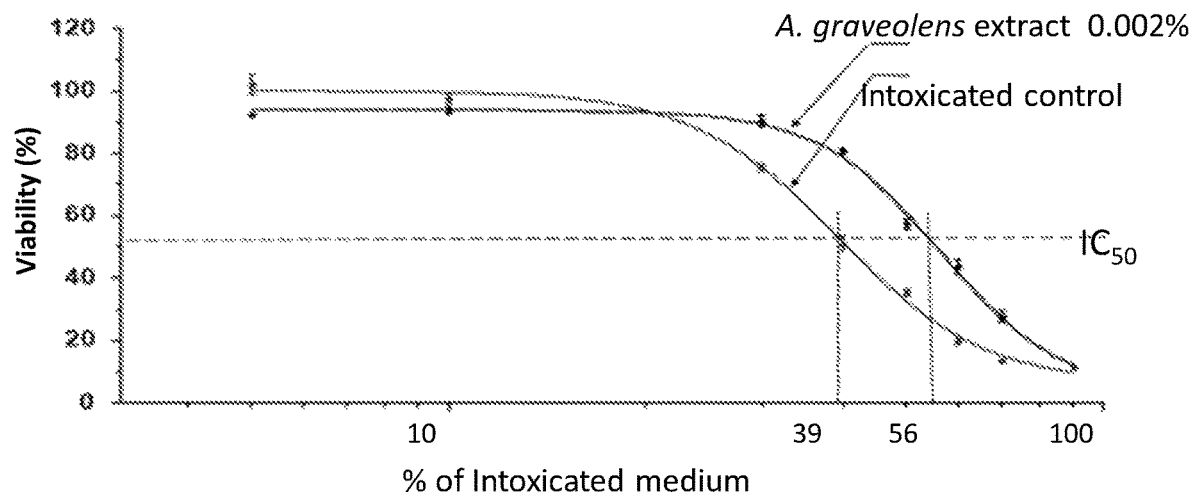

All experimental conditions were performed in n=5, except for non-intoxicated control performed in n=10. As is shown in FIG. 1, the extract, tested at a concentrations as low as 0.001% (FIG. 1A) and 0.002% (FIG. 1B) had a clear protecting effect against cigarette smoke-induced intoxication, with a marked shift of the IC50 value from 39.3% under the control conditions to 48.5 and 56.3% at 0.001% and 0.002% extract, respectively.

Example 4: Effect of an *Asteriscus graveolens* Extract on Gene Expression in Keratinocytes

*Asteriscus Graveolens* extract was produced as described in Example 1 and used for evaluating its effect on gene expression profile. Human Normal Epidermal Keratinocyte (NHEK) cells were treated for 24 h with either 0.01% *Asteriscus Graveolens* extract or $H_2O$ as control both diluted in assay medium. mRNA was then extracted from the treated cells, translated to a double stranded cDNA and loaded on an Affymetrix U219 array kit for transcriptomic profile. Among 30,000 tested genes, 211 were found to be significantly modulated demonstrating an expression level above or below a cutoff of 2 fold change.

Table 2 shows genes the expression of which was altered as a result of treatment with *Asteriscus* extract fraction. The biological phenomena affected from the observed reduction or elevation in the gene expression are also indicated.

TABLE 2

Effect of *Asteriscus graveolens* extract on gene expression in cells

| Gene Name | Fold-regulation* | Biological effect |
|---|---|---|
| USP15 | 0.27 | Increase NRF2, which serve as the key transcriptional activator of anti-oxidant genes |
| ATF6 | 0.31 | Reduced cell death mediated by ER stress known to occur following exposure to Cigarette Smoke |
| MAPKAPK2 | 0.34 | Reduced expression of key inflammatory cytokines known to induce inflammation and cell death |
| ENC1 | 0.38 | Increase NRF2 and the transcription of anti-oxidant genes |
| YWHAE | 0.39 | Anti-apoptotic activity following DNA damage known to occur following exposure to Cigarette smoke (CS) |
| NFIX | 0.25 | Stem cell survival |
| USP15 | 0.27 | Wound healing; antioxidant response |
| IL6ST | 0.3 | Anti-inflammatory |
| ACER3 | 0.32 | Improving skin barrier |
| SCRN1 | 0.33 | Anti-allergic |
| CYP4F11 | 2.03 | Toxin metabolism |

*The fold regulation is the ratio of gene expression signal of *Asteriscus* treated cells to signal of untreated cells.

The results establish that the *Asteriscus graveolens* extract increases skin's inherent defenses by modulating gene expression as to regulate pathways associated with pollution and toxicity such as inflammation, oxidative stress, endoplasmic reticulum (ER) stress and cell death.

Example 5: Effect of Various Concentrations of *A. Graveolens* Extract on Smoke-Challenged Lung Epithelial Cells

*Asteriscus Graveolens* was harvested from two of its known habitats at different time points. One plant termed AS1-81-1 was harvested from the Dead Sea on April 2014 while the second one termed AS1-91-1 was harvested from the Arava on June 2015. Both plants were extracted as in Example 1 and evaluated for cell viability of epithelial cells derived from lung following exposure to cigarette smoke condensate.

Lung derived epithelial cells were treated with various concentrations of *Asteriscus Graveolens* and cell viability was determined following exposure to either 0.4 mg/ml or 0.24 mg/ml of cigarette smoke condensate (CSC). CSC is a commercial product comprising cigarette smoke ingredients in DMSO solution (Murty Pharmaceuticals LTD).

Cells were treated with *Asteriscus Graveolens* extract for 24 hours followed by treatment with CSC (0.4 mg/ml, 0.24 mg/ml) in the presence of *Asteriscus Graveolens* for additional 24 hours. Cell viability was then evaluated using WST1 method (similar to MTT). In brief, WST-1 is added directly in to the medium of the growing cells. The stable tetrazolium salt WST-1 is then cleaved to a soluble formazan in a reduction process mediated by the glycolytic product NAD(P)H forming a red colored solution. The obtained optical density of the red solution is proportional to the viability of the cells and measure in a wave length of 450 nm.

Figure 8A:
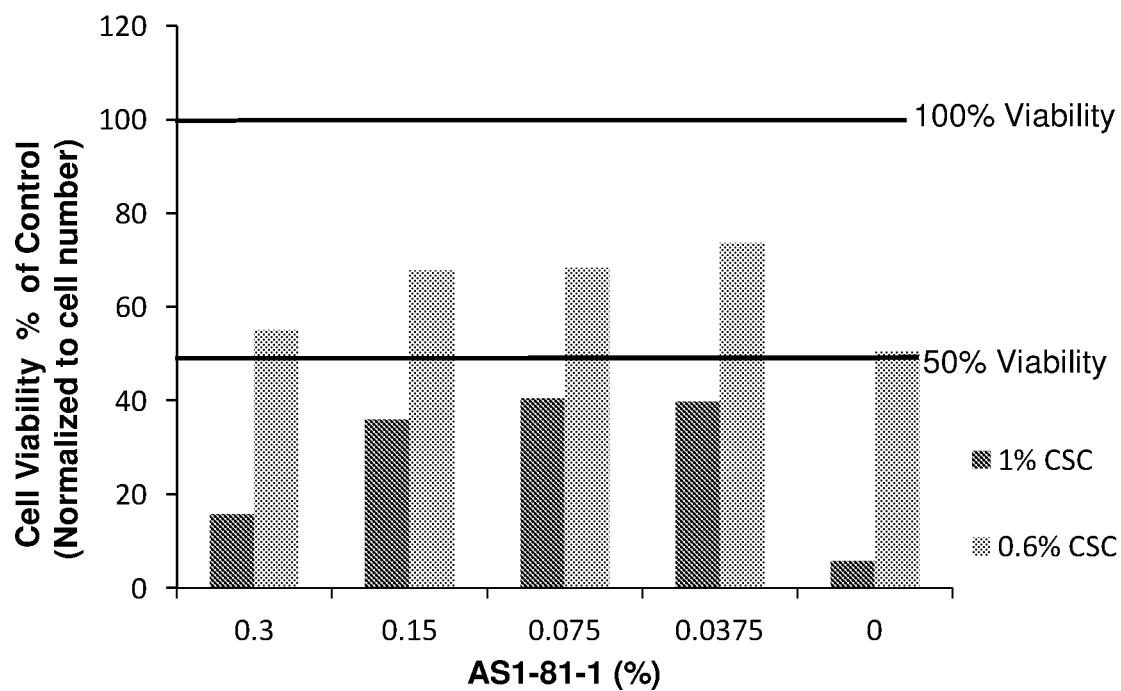
FIG. 8 demonstrates the protective effect of two preparations of *A. graveolens* extract (AS1-81-1, FIG. 8A and AS1-91-1, FIG. 8B) on lung derived cells following exposure to cigarette smoke condensate (CSC).
Figure 8B:
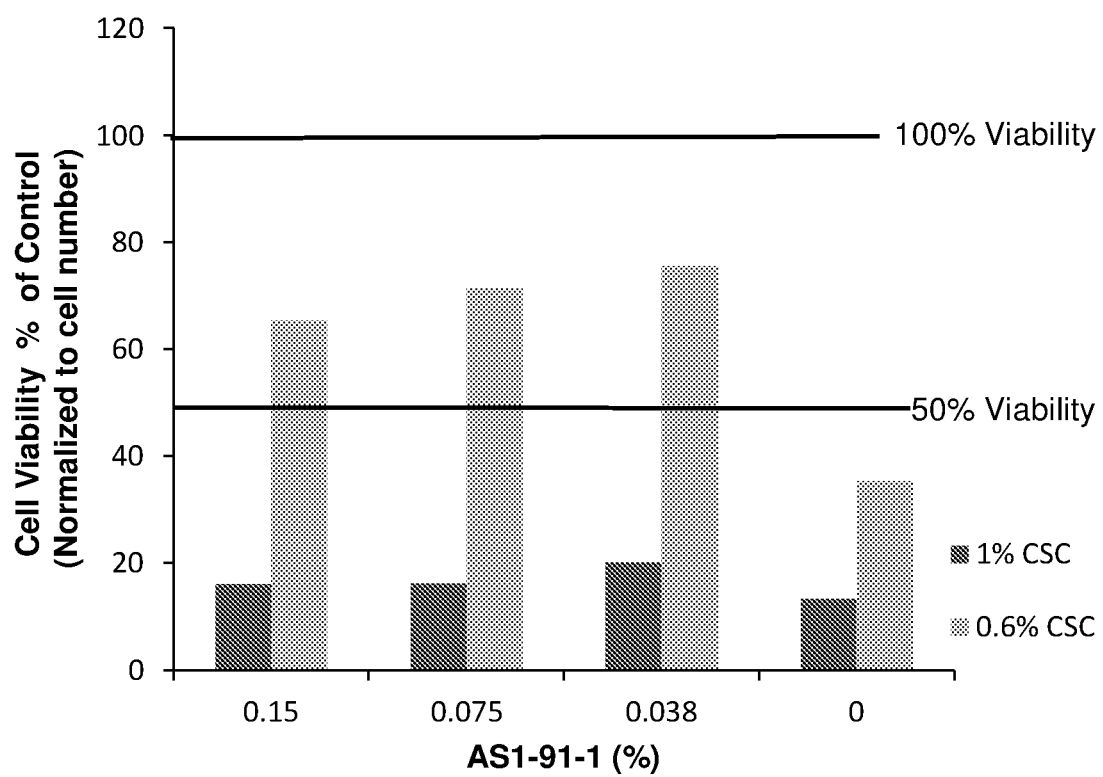

FIG. 8 demonstrate that the two extract preparation have a protective effect on epithelial lung tissue from smoke pollutants.

In this assay, the protective effect was significant at extract concentration of 0.038%-0.3% for AS1-81-1 and 0.038%-0.15% for AS1-91-1.

Figure 2A:
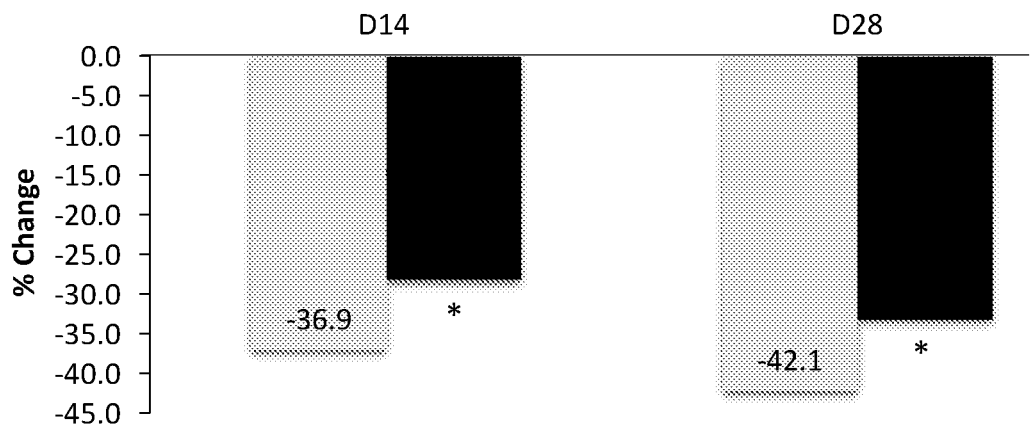
FIG. 2 demonstrates that *A. graveolens* extract has an anti-ageing effect. The wrinkle count (FIG. 2A) and wrinkle volume (FIG. 2B) were tested for the extract (light bars) or placebo (dark bars) treatments. The percentage change was measured after 14 and 28 days as indicated. Significant change is marked with asterisk (*).
Figure 2B:
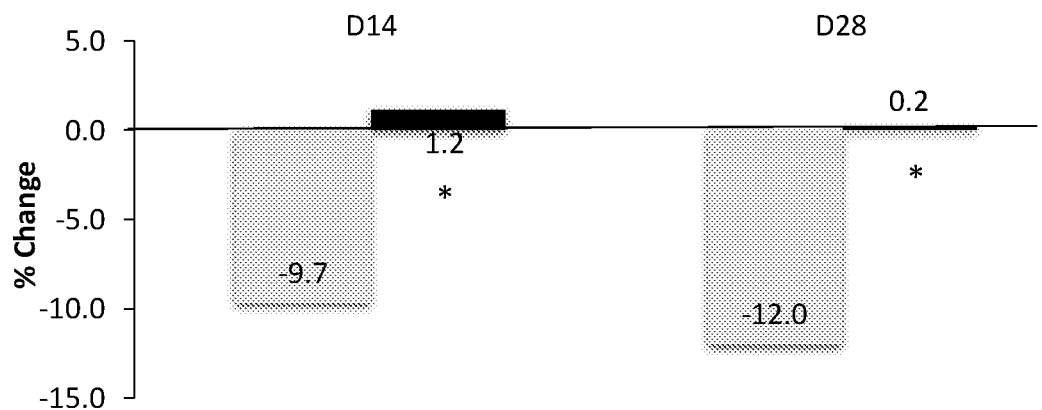
Figure 3:
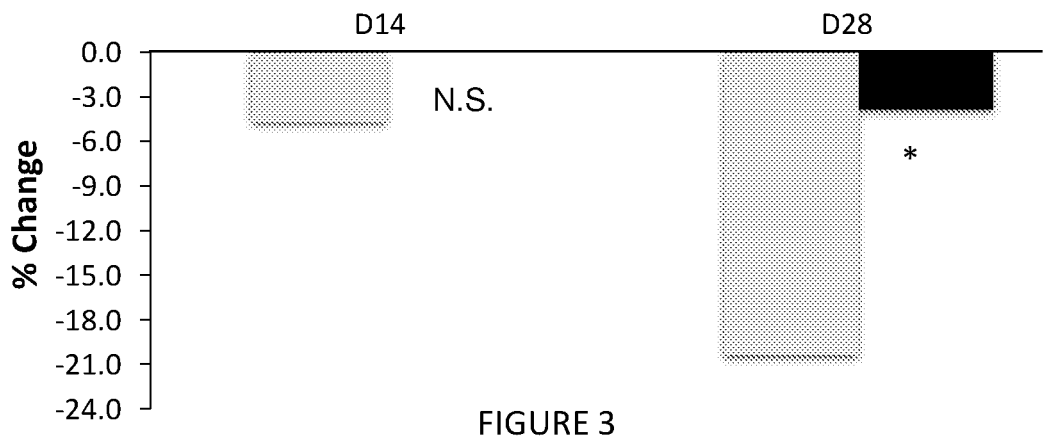
FIG. 3 shows the clinical evaluation of wrinkles treated with *A. graveolens* extract. The wrinkle grey scale (WGS) was evaluated for the extract (light bars) and placebo (dark bars). The percentage of change was measured after 14 and 28 days as indicated. Significant change is marked with asterisk (*). NS—Not significant.
Figure 4A:
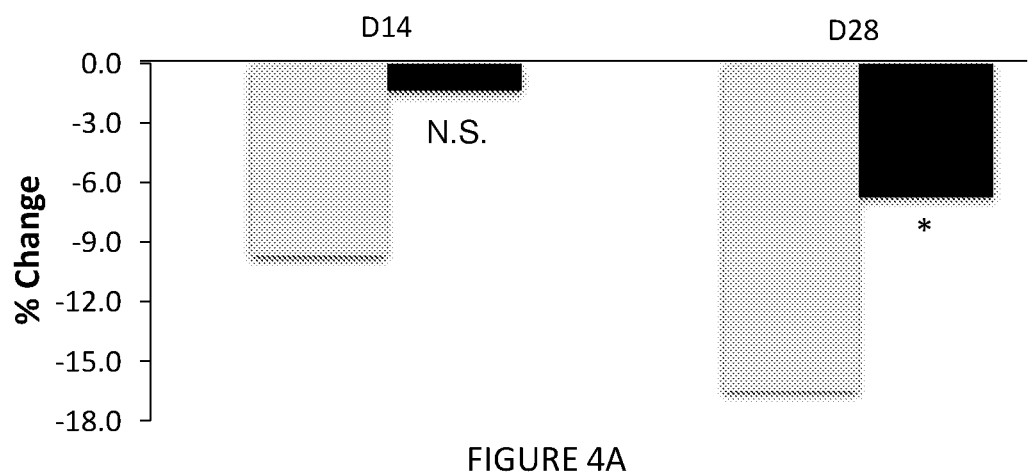
FIG. 4 shows clinical evaluation of skin treated with *A. graveolens* extract. Skin roughness (FIG. 4A) and skin texture (FIG. 4B) were evaluated for the extract (light bars) and placebo (dark bars). The percentage change was measured after 14 and 28 days as indicated. Significant change is marked with asterisk (*). NS—Not significant.
Figure 4B:
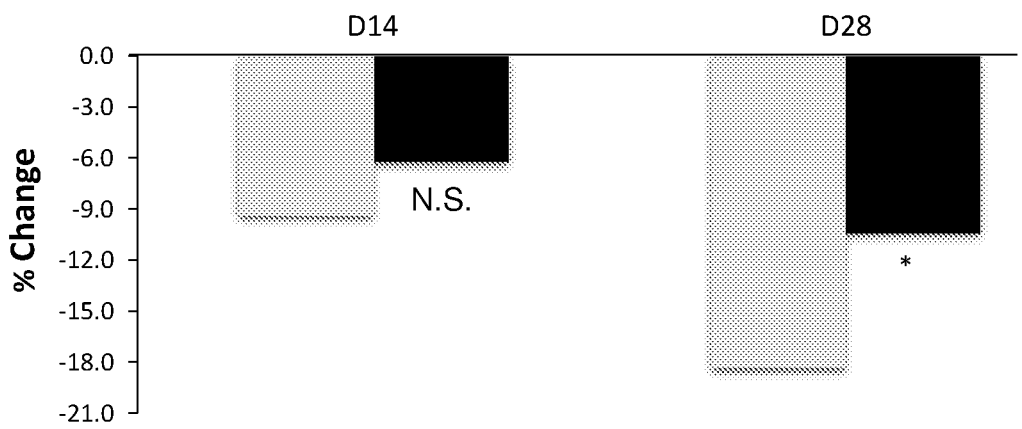
Figure 5:
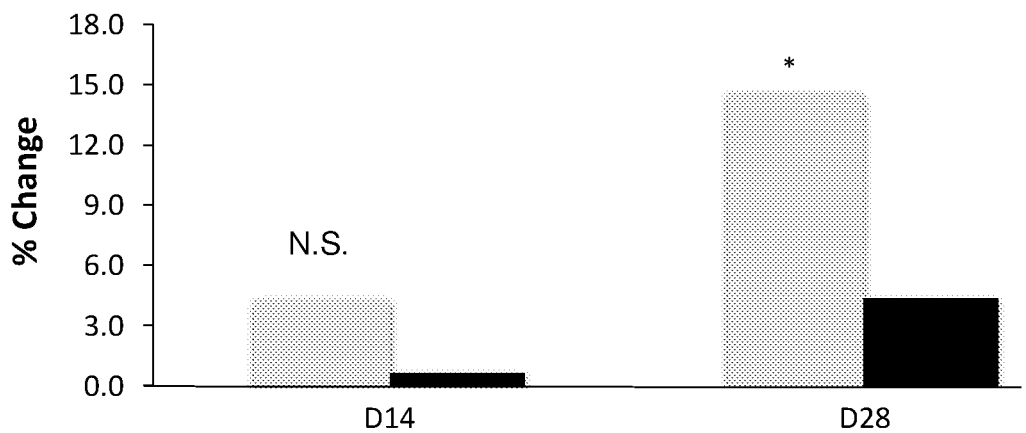
FIG. 5 shows the effect of *A. graveolens* extract on skin color. Skin color was evaluated by Individual Typological Angle (ITA) units, calculated from L* (increase in brighter skin) and b* (decrease in yellow skin). ITA was evaluated for the extract (light bars) and placebo (dark bars). The percentage change was measured after 14 and 28 days as indicated. Significant change is marked with asterisk (*). NS—Not significant.
Figure 6:
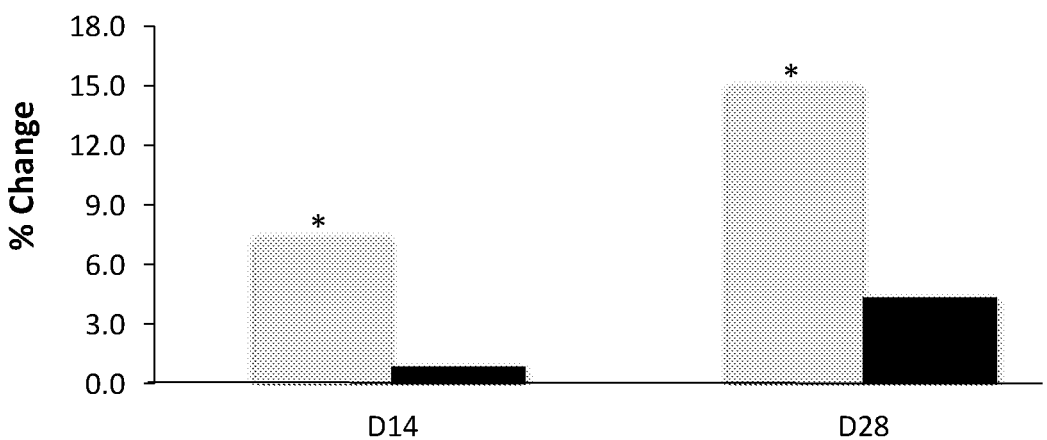
FIG. 6 shows the change in skin hydration of skin treated with *A. graveolens* extract. Skin hydration was evaluated for the extract (light bars) and placebo (dark bars). The percentage change was measured after 14 and 28 days as indicated. Significant change is marked with asterisk (*).
Figure 7:
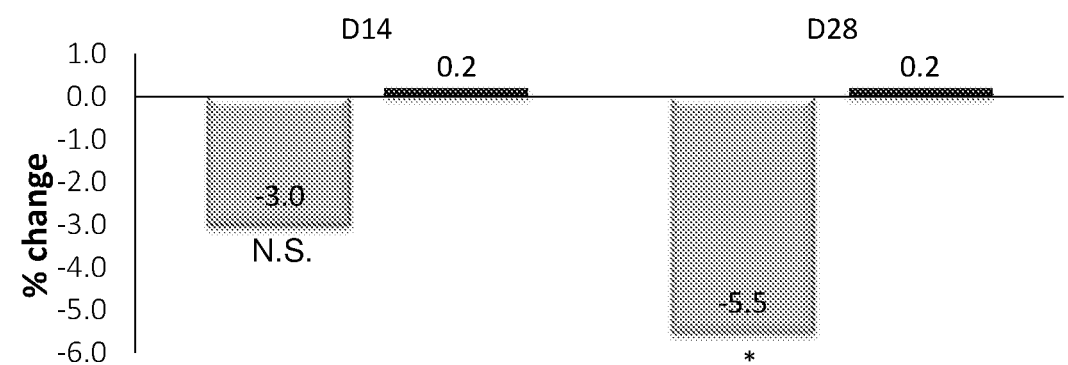
FIG. 7 shows change in visible spot counts on skin treated with *A. graveolens* extract. Visible spot counts were examined for the extract (light bars) and placebo (dark bars). The percentage change was measured after 14 and 28 days as indicated. Significant change is marked with asterisk (*). NS—Not significant.

Example 6: Clinical Evaluation of the Effect of *Asteriscus graveolens* Extract on Skin Parameters A clinical study was performed to substantiate in-vivo the *Asteriscus* extract's activity as a 'detoxifying' agent, expected to manifest as global anti-aging benefits resulting from enhanced resistance of the skin to chronic toxic insult.
Study Design:
  Double blind, test compound of cream-gel chassis containing 1% *A. graveolens* extract (produced as described in Example 1 hereinabove) vs. placebo (cream-gel chassis only).
  Age distribution: 46-60; Group size=25; all-female.
  Subjects with 'heavy smoking habits' (>10 cigarettes/day), and 'with ageing signs' in the periocular area and the corner of the mouth.
  Split-face (left/right) application twice daily for 4 weeks, with measures at D0, D14, and D28.
  Measures:
    Visia CA: standardized imaging with normal, cross-polarized, and UV illumination.
    Wrinkles and roughness evaluation by Primos 3D.
    Skin hydration by Corneometer.
    Skin elasticity by Cutometer.
    Skin color (as L, a, b) by colorimeter (Minolta).
    Clinical assessment by a trained clinician, under standardized 'daylight' illumination—wrinkles (picture-based scale), roughness, suppleness, evenness of complexion, texture.
    Subjective self-assessment by questionnaire.
The study was carried out at PhD laboratories (Portugal)—PhD labs study number 2260115.
Results:
Anti-Aging (Anti-Wrinkle):
  The compound of the invention exhibits good anti-aging efficacy, expressed as a strong and significant reduction in wrinkle count, as well as a significant reduction in wrinkles volume. As shown in FIG. 2A, the wrinkles count was reduced by 36.9% at day 14 and by 42.1% at day 28 as compared to decrease of 28% on day 14 and 33% on day 28 in control (placebo). The wrinkles volume was reduced by 9.7% on day 14 and by 12% on day 28 as compared to an increase of 1.2% on day 14 and of 0.2% on day 28 in skin areas treated with the placebo (FIG. 2B).
Clinical Evaluation of Wrinkles:
  Confirming the instrumental measurements above, clinical evaluation revealed a significant anti-aging effect, expressed as a significant reduction in wrinkle score (4.7% on day 14 and 20.3% on day 28) vs. baseline and placebo (placebo showed 3.8% decrease on day 28, FIG. 3).
Clinical Evaluation, Additional Parameters:
  Use of the test compound comprising *A. graveolens* resulted in:
    A moderate but significant improvement in skin roughness grades (vs. baseline and placebo, FIG. 4A).
    A moderate but significant improvement in skin texture grades (vs. baseline and placebo, FIG. 4B).
    A small but significant improvement in skin evenness grades (vs. baseline and placebo).
  In all three cases, the data showed a clear time dependence (significant at day 28 but not at day 14).
Skin Color (Chromometer):
  Use of the test compound comprising *A. graveolens* extract of the invention resulted in a small but significant lightening effect (vs. baseline and placebo), manifested in an increase in L* (i.e. brighter skin), and a decrease in b* (i.e. less yellow skin). The Individual Typological Angle (ITA), calculated from L* and b*, shows a corresponding increase (lighter skin). The changes observed (2 units of L*, half a unit of b*) represents noticeable changes in skin tone (FIG. 5).
  Without wishing to be bound by any specific theory or mechanism of action, this effect may be due to a detoxification mechanism: chronically challenged skin (like a heavy smoker's facial skin or skin under chronic, low-grade inflammatory conditions) will generate elevated melanin levels, resulting in elevated or uneven skin pigmentation, spots, etc. The composition of the present invention appears to alleviate this effect. The activity is only detectable at day 28, consistent with an effect which requires time for the desquamation process to dispose existing melanin-loaded keratinocytes/corneocytes, to be replaced by new cells which came to maturity under the influence of *A. graveolens* extract and therefore under lower chronic toxic stress.
  Skin Hydration (Corneometer):
    The *A. graveolens* extract of the invention showed a time-dependent increase in skin hydration, statistically significant vs. baseline and placebo (placebo has no significant activity). The skin hydration was measured at the corner of the mouth (FIG. 6).
    Visia: Skin treated with *A. graveolens* extract showed a statistically significant improvement in skin tone shown by a reduction in the counts of UV and visible spots (FIG. 7).
    Cutometer:
    The plant extract of the invention also had a positive effect on the firmness of the skin.
    Self-Evaluation Questionnaire:
    The *A. graveolens* plant extract of the invention further improved skin parameters such as skin tone, skin radiance, occurrence of spots, skin sensitivity, and wrinkles as reflected by self estimation of subjects treated with the extract of the invention. A set of 16 questions regarding variety of skin parameters was used to evaluate the treatment effect. Self assessment of improvement after 28 days of treatment was higher in subjects treated with the compound of the invention as compared to placebo.
General Comment on Time-Dependency:
  In many of the cases, the effects observed are suggested or already visible at D14, but become stronger or acquire statistical significance at D28. Without wishing to be bound by any specific theory or mechanism of action, these results support a repair mechanism induced by *A. graveolens*, inducing cell intrinsic, active processes resulting in a relief of some of the chronic toxic stress effects on the skin, allowing it to gradually return to a more favorable homeostasis state—translating into visible beauty benefits.

Example 7: Cosmetic Formula Comprising *Asteriscus graveolens* Extract

Table 3 below shows a representative composition comprising *Asteriscus graveolens* extract for cosmetic use.

TABLE 3

Representative cosmetic composition comprising *Asteriscus graveolens* extract

| INCI/chemical name | Tradename | % |
|---|---|---|
| Water | Water | 84.35 |
| Butylene glycol | 1,3-butanediol | 4.00 |
| Dipropylene glycol | Dipropylene glycol | 1.00 |
| Hexylene glycol | Hexylene glycol | 1.00 |
| Polysorbate 20 | Tween 20 | 1.00 |
| Hydrogenated polydecene | Nexbase | 1.50 |
| Cyclomethicone | SF0005Z | 4.00 |
| *Asteriscus graveolens* extract (produced as in Example 1 hereinabove) | | 1.00 |
| Glycerol | Glycerin | 0.00 |
| Carbomer | Carbopol 940 | 0.80 |
| Triethanolamine | Triethanolamine | 0.70 |
| Phenoxyethanol | Phenoxyethanol | 0.40 |
| Methyl paraben | Nipagin M | 0.15 |
| EDTA | EDTA | 0.10 |
| FD&C blue 1 | Erioglaucine | 0.000000 |
| FD&C Red 20 | Allura Red AC | 0.000000 |
| FD&C Yellow 5 | Tartrazine | 0.000000 |
| TOTAL | | 100.00 |

Process (Laboratory Scale):
1. Preservatives/polyols premix: the following are combined with stirring at 45° C. until complete dissolution: Butylene glycol; Hexylene glycol; Dipropylene glycol; Phenoxyethanol; Methyl paraben.
2. Organic phase: the following are combined with stirring at 45° C. until complete mixing: Cyclomethicone; Hydrogenated Polydecene.
3. Main mix:
   a. The Carbomer is dispersed into the Water (84.35% formula weight) at 45° C., slowly and with vigorous agitation. Agitation is continued until the carbomer is fully dispersed.
   b. The resulting mixture is homogenized.
   c. The following are added in sequence: EDTA; Tween 20; Preservatives/polyols premix; Organic phase.
   d. Triethanolamine is added till pH=5.5-6.5.
   e. Stirring is continued for 10 min
4. Active:
   i. *Asteriscus Graveolens* extract (100% extract prepared as described in Example 1 hereinabove) is added with stirring to the base mix.
   ii. The resulting mixture is homogenized.

Example 8: Effect of the *Asteriscus graveolens* Extract on DNA Damage

Human alveolar basal epithelial cells were used as model system. A549 cells were cultured in a culture medium and the medium was then removed and replaced by a medium containing 0.05%, 0.16% and 0.5% of the *A. graveolens* plant extract produced as described in Example 1 hereinabove. The cells were incubated in the extract-containing medium overnight, and then the medium was removed and replaced with a culture medium intoxicated with cigarette smoke condensate (CSC), being a model for urban air pollution. The culture was further incubated with the intoxicated medium for additional 24 h or 48 h. Based on a previous calibration assays, two concentrations of CSC were examined, 100 µg/ml and 200 µg/ml.

Figure 9:
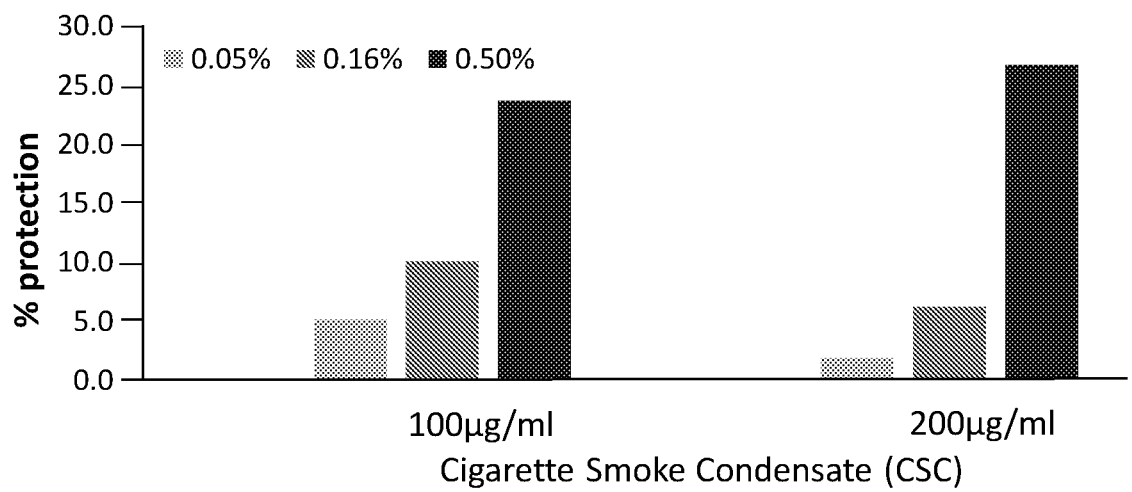
FIG. 9 demonstrates the protective effect of *A. graveolens* extract on alveolar basal epithelial cells from DNA fragmentation caused by cigarette smoke condensate (CSC) as measured by TUNEL assay.

Following the incubation with CSC, the medium was removed and the cells were analyzed for DNA fragmentation using TUNEL (Terminal deoxynucleotidyl transferase dUTP nick end labeling) assay according to the manufacturer protocol. The TUNEL assay is based on DNA fragmentation occurring during apoptosis following the activation of endonucleases. The labeling of the 3' ends of DNA fragments provides an easy measure of cells undergoing apoptosis. Modified nucleotides are incorporated at the 3' ends by the activity of terminal deoxynucleotidyl transferase (TdT). These nucleotides are detected using a horseradish-peroxidase detection system and a non-toxic colorimetric substrate. As is shown in FIG. 9, the *A. graveolens* plant extract fraction of the invention protected alveolar basal epithelial cells from DNA fragmentation caused by CSC in a dose-dependent manner.

The protective effect of the extracts of the invention on DNA was further examined using 8-hydroxy-2'-deoxyguanosine (8-OHdG) assay, measuring oxidative damage of DNA.

8-hydroxy-2'-deoxyguanosine (8-OHdG or 8-oxo-dG) is an oxidized derivative of deoxyguanosine and is generated by hydroxyl radicals, singlet oxygen, and one-electron oxidants in cellular DNA.

Figure 10:
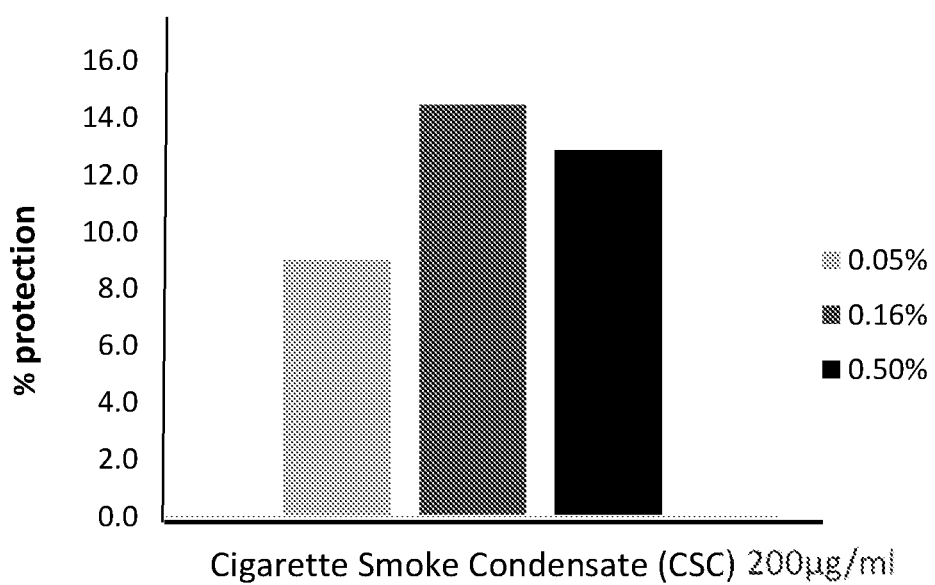
FIG. 10 demonstrates the protective effect of *A. graveolens* extract on alveolar basal epithelial cells from DNA fragmentation caused by cigarette smoke condensate (CSC) as measured by 8-hydroxy-2'-deoxyguanosine (8-OHdG) assay.

Following exposure to 200 µg/ml CSC (with varying amounts of the *A. graveolens* plant extract fraction of the invention (experiment carried out as described above), the cells were lysed and total DNA collected. Single stranded DNA was prepared and used in the assay. The assay measures the amount of 8-oxo-dG bases produced as a result of exposure to the cigarette smoke condensate, and a decrease in the values recorded imply a reduction in DNA damage. As shown in FIG. 10, *A. graveolens* plant extract fraction of the invention led to moderate protection of alveolar basal epithelial cells from DNA fragmentation caused by CSC.

Example 9: Evaluation of the Ocular Irritant Potential of *A. graveolens* Extract Using the HET-CAM Assay A Hen's Egg Test-Chorioallantoic Membrane (HET-CAM) assay was performed based on INVITTOX PROTOCOL Number 47 (1990), ISSN #0960-2194.

Test System Justification:

The HET-CAM has been shown to be a qualitative method of assessing the potential irritancy of chemicals. The CAM is a complete tissue containing arteries, veins and capillaries, and is technically easy to study. It responds to injury with an inflammatory process similar to what one would observe in the conjunctival tissue of a rabbit's eye. Its well-developed vascularization provides an ideal model for ocular irritation studies.

Fertile, 10 day old, white Leghorn eggs are used in the HET-CAM as an alternative to the Draize Rabbit Eye Test and are configured to accommodate 6 test groups—3 test article concentrations, 2 positive controls and 1 vehicle control group.

Development: eggs were placed in commercial incubators. On day 10 of development, eggs were removed from the incubator and candled to determine the viability of the embryo. A rectangular window was removed from the shell directly over the air cell and the egg membrane was carefully moistened with 2-3 ml 0.9% saline and returned to the incubator.

Test items were then applied to the eggs, left on for a defined (20-second) exposure period, and rinsed with saline solution. The eggs were observed continuously for 5 minutes for the appearance of lysis, hemorrhaging and/or coagulation.

The eggs were scored for severity at 1 and 5 minutes. The severity of each reaction after 1 and 5 minutes was recorded.

In this model, an *Asteriscus Graveolens* extract fraction prepared as described in Example 1 hereinabove (containing 50% glycerin), tested at 5% dilution, was considered to be slightly irritant (total irritation score 2.0).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for protecting a tissue comprising epithelial cells from the deleterious effect of at least one pollutant comprising:
   topically administering to a skin of a subject in need thereof a composition comprising an effective dose of a polar solvent extract derived from *Asteriscus graveolens* plant, a fraction thereof or any combination of a polar solvent extract derived from *Asteriscus graveolens* plant and a fraction thereof, so as to result in protecting the tissue from the at least one pollutant, wherein the at least one pollutant originates from at least one of combustion gas, industrial pollution and smoke.

2. The method of claim 1, wherein the effective dose is from 0.1% to 10% w/w relative to the total weight of the composition.

3. The method of claim 1, wherein the smoke is tobacco smoke.

4. The method of claim 1, wherein a test, to determine whether the composition results in protecting the tissue from the at least one pollutant comprises
   culturing epithelial cells in different concentrations of cigarette smoke-intoxicated medium containing the composition; and
   measuring epithelial cell viability in the different concentrations of cigarette smoke-intoxicated medium containing the composition,
   wherein there is an increase in $IC_{50}$,
   wherein the increase represents an increase in the dose of the cigarette smoke-intoxicated medium necessary to have a significant toxic effect, representing a protective effect of the composition.

5. The method of claim 1, wherein protecting the skin from the deleterious effect of the at least one pollutant results in at least one outcome selected from the group consisting of increased skin cell viability, improved skin appearance, reduced premature skin aging and any combination thereof.

6. The method of claim 5, wherein improved skin appearance and/or reduced premature skin aging comprises reduction in the appearance of at least one of wrinkles, brown spots and red spots of the skin.

7. The method of claim 1, wherein the polar solvent is water.

8. The method of claim 1, wherein the polar solvent comprises water and at least one additional polar solvent.

9. The method of claim 8, wherein the at least one additional polar solvent is selected from the group consisting of glycerin, ethanol, propylene glycol, butylene glycol, methanol, and acetone.

10. The method of claim 9, wherein the polar solvent comprises water and glycerin.

11. The method of claim 10, wherein the polar solvent extract and/or fraction thereof is in a form of a solution comprising 40 to 60% (w/w) glycerin.

12. The method of claim 1, wherein the polar solvent extract or a fraction thereof is essentially devoid of essential oils.

13. The method of claim 1, wherein the composition further comprises an additional active agent selected from the group consisting of an anti-oxidant, a chelator, a cleansing agent, a skin protectant, a sunscreen, a skin lightening agent, an anti-wrinkling agent, an anti-inflammatory agent, an anti-aging agent, and any combination thereof.

14. The method of claim 1, wherein the composition is a cosmetic composition formulated for topical administration to the skin.

* * * * *